(12) United States Patent
Gill et al.

(10) Patent No.: US 7,987,056 B2
(45) Date of Patent: Jul. 26, 2011

(54) MIXED-LIBRARY PARALLEL GENE MAPPING QUANTITATIVE MICRO-ARRAY TECHNIQUE FOR GENOME-WIDE IDENTIFICATION OF TRAIT CONFERRING GENES

(75) Inventors: Ryan T. Gill, Boulder, CO (US); Michael D. Lynch, Westminster, CO (US); Tanya Warnecke, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 515 days.

(21) Appl. No.: 11/231,018

(22) Filed: Sep. 20, 2005

(65) Prior Publication Data

US 2006/0084098 A1    Apr. 20, 2006

Related U.S. Application Data

(60) Provisional application No. 60/611,377, filed on Sep. 20, 2004.

(51) Int. Cl.
*G06F 19/00* (2006.01)
*C12Q 1/68* (2006.01)
*C12N 15/00* (2006.01)

(52) U.S. Cl. ............... 702/20; 435/6; 435/320.1
(58) Field of Classification Search .......... None
See application file for complete search history.

(56) References Cited

U.S. PATENT DOCUMENTS

| | | |
|---|---|---|
| 4,458,066 A | 7/1984 | Caruthers et al. |
| 4,683,202 A | 7/1987 | Mullis |
| 5,256,648 A | 10/1993 | Gasparro et al. |
| 5,484,908 A | 1/1996 | Froehler et al. |
| 5,543,507 A | 8/1996 | Cook et al. |
| 5,672,593 A | 9/1997 | Michejda et al. |
| 5,681,941 A | 10/1997 | Cook et al. |
| 6,068,977 A * | 5/2000 | Perlin ................ 506/4 |

OTHER PUBLICATIONS

Zhang et al., Construction and characterization of two rice bacterial artifical chromosomelibraries from the parents of a permanent recombinant inbred mapping population, Molecular Breeding, 1996, 2, 11-24.*
Li et al., Characterization of quantitative trait loci (QTLs) in cultivated rice contibuting to field reistance to sheath blight (Rhizoctonia solani), Theor Appl Genet, 1995, 91, 382-388.*
Quackenbush, Nature Reviews, Genetics, Computational Analysis of Microarray Data, 2001, 2, 418-427.*
Rondon et al. (PNAS, 1999, 96, 6451-6455).* Markie et al., (Somatic Cell and Molecular Genetics, 1993, 19(2), 161-169).*
Lio et al., (Bioinformatics Review, 2003, 19(1), 2-9).*
Liu et al. (Gene, 2002, 282, 247-255).*
Gill, Ryan T. et al. Genome-wide screening for trait conferring genes using DNA microarray. PNAS. May 14, 2002, 7033-7038. vol. 99, isu. 10. NAS of USA.

* cited by examiner

*Primary Examiner* — Marjorie Moran
*Assistant Examiner* — Larry D Riggs, II
(74) *Attorney, Agent, or Firm* — Joseph Fischer

(57) ABSTRACT

The present disclosure concerns methods and compositions relating to mixed-library parallel gene trait mapping. In particular embodiments, the methods concern quantitative microarray hybridization techniques for genome-wide identification of trait conferring genes. In other embodiments, the compositions concern genetic elements that confer or are associated with a trait. In an exemplary embodiment, the trait is enhanced growth rate. In another exemplary embodiment, genetic elements that confer enhanced bacterial growth rate comprise part or all of the sequences of SEQ ID NO:1, SEQ ID NO:2, SEQ ID NO:3, SEQ ID NO:4 or SEQ ID NO:5. In other embodiments, the genetic elements that confer enhanced bacterial growth rate correspond to the YliF, adrA, yeaP, yddV or ydeH genes of *E. coli*.

28 Claims, 10 Drawing Sheets

*FIG. 8*

| TABLE 1. | | | | |
|---|---|---|---|---|
| Plasmid | Genome Segment Represented | Scale Represented | Average Maximal Growth Rate | Relative Growth Rate |
| | | | hr-1 | to vector |
| None (Mach1 T1 no vector) | NA | NA | 0.398 | 1.932 |
| pSmart-LCKan | NA | NA | 0.206 | 1.000 |
| pSLCK-yli-op-1 | moeA-yliG | 12000 | 0.281 | 1.366 |
| pSLCK-yli-op-2 | moeA-yliG | 12000 | 0.247 | 1.200 |
| pSLCK-yli-op-3 | ? | 8000 | 0.297 | 1.444 |
| pSLCK-yli-op-4 | ? | 8000 | 0.323 | 1.571 |

SEQUENCE LISTING

<160> NUMBER OF SEQ ID NOS: 7

<210> SEQ ID NO 1
<211> LENGTH: 11837
<212> TYPE: DNA
<213> ORGANISM: Escherichia coli

<400> SEQUENCE: 1

```
ctctgcggta gtcaggcgag ttcccgccgg gaaacaacc gcacctgcag agatatcttc      60
accgcgacgg cgaatatttt gcccgctacg cacttcagca gtaaaacgca cgccattgtc     120
catttgttca gtctgctcct gcatcaccac cgcttcgcag ccttccggca ccggcgcacc     180
ggtcataata cgaatgcagg tacccgcagg ccattcacca tggtatggct gaccggcaaa     240
ggatttaccg gcaacgggca gcggttgccc ggaggcaata tcggctaaac gcaccgcgta     300
gccgtccatt gcggagttat caaacccccgg aacatcaagc ggcgaaacga catcgctcgc     360
cagaatacga ccaaaacact gtaccagtgg cagcgtttcc tgggcggtca gtggggtgac     420
```

```
gcgagaaagc atctcattaa gcgcggtgtc gagcgacatc aatccggtgg taaattccat    480
gaaaacactc ctgcggaggc aaaatcgaat ttgcctatta tgtcagaaaa acgccacaga    540
ctgtatgcca cctcgggcgt agcgctgggt cctgcctttta catgccatat ccatctttct    600
atattcaaaa attgaatgag taattcataa aaattctgat atttatagca aaagtggcga    660 accacccctta atgacgaat actatgggca aagcagtcat tgcaattcat ggtggcgcag    720
gtgcaattag ccgcgcgcag atgagtctgc aacaggaatt acgctacatc gaggcgttgt    780
ctgccattgt tgaaaccggg cagaaaatgc tggaagcggg cgaaagtgcg ctggatgtgg    840
tgacggaagc ggtgcgtctg ctggaagagt gtccactgtt aacgccgga attggcgctg    900 tctttacgcg tgatgaaacc catgaactgg acgcctgtgt gatggatggt aacaccctga    960
aagccggtgc ggtggcgggc gttagtcatc tgcgtaatcc ggttcttgcc gcccggctgg   1020
tgatggagca aagcccgcat gtgatgatga ttggcgaagg ggcagaaaat tttgcgtttg   1080
ctcgtggcat ggagcgcgtc tcgccggaga ttttctccac gtctttgcgt tatgaacaac   1140
tactggcagc gcgcaaggaa ggggcaaccg tcctcgacca tagcggtgcg ccactggatg   1200
aaaaacagaa aatgggcacc gtgggggccg tggcgttgga tttagacggc aatttggcgg   1260
cagccacgtc cacaggcgga atgaccaata aattacccgg acgagttggc gatagtccct   1320
tagtgggtgc cggatgctac gccaataacg ccagtgtggc ggtttcttgt accggcacgg   1380
gcgaagtctt catccgcgcg ctggcggcat atgacatcgc cgcgttaatg gattacggcg   1440
gattaagtct cgcggaagcc tgcgagcggg tagtaatgga aaaactccct gcgcttggcg   1500
gtagcggtgg cttaatcgct atcgaccatg aagggaatgt cgcgctaccg tttaacaccg   1560
aaggaatgta tcgcgcctgg ggctacgcag gcgatacgcc aaccaccggt atctaccgtg   1620
aaaaagggga caccgttgcc acacagtgat gaacttgatg ccggtaatgt gctggcggtt   1680
gaaaatctga atattgcctt tatgcaggac cagcagaaaa tagctgcggt ccgcaatctc   1740
tcttttagtc tgcaacgcgg tgagacgctg gcaattgttg gcgaatccgg ctccggtaag   1800
tcagtgactg cgttggcatt gatgcgcctg ttggaacagg cgggcggttt agtacagtgc   1860
gataaaatgc tgttgcagcg gcgcagtcgc gaagtgattg aacttagcga gcagaacgct   1920
gcacaaatgc gccatgttcg cggtgcggat atggcgatga tatttcagga gccgatgaca   1980
tcgctgaacc cggtatttac tgtgggtgaa cagattgccg aatcaattcg tctgcatcag   2040
aacgccagtc gtgaagaagc gatggtcgag gcgaagcgga tgctggatca ggtacgcatt   2100
cctgaggcac aaaccattct ttcacgttat ccgcatcaac tctctggcgg gatgcgccag   2160
cgagtgatga ttgcgatggc gctgtcatgc cgcccggcgg tgctgattgc cgatgagcca   2220
accaccgcgc tggatgtcac tattcaggcg cagatcctgc aattaatcaa agtattgcaa   2280
aaagagatgt cgatgggcgt tatctttatc actcacgata tgggcgtggt ggcagagatt   2340
gccgatcggg tactggtgat gtatcaggcc gaggcggtgg aaacgggtac cgtcgaacag   2400
atttttcatg caccgcaaca tccttacacc cgtgcgctgt tagctgctgt tccgcaactt   2460
ggtgcgatga aagggttaga ttatccccga cgtttcccgt tgatatcgct tgaacatcca   2520
gcgaaacagg cccccccccat cgagcagaaa acggtggtgg atggcgaacc tgttttacga   2580
gtgcgtaatc ttgtcacccg tttccctttg cgcagcggtt tgttgaatcg cgtaacgcgg   2640
gaagtgcatg ccgttgagaa agtcagtttt gatctctggc ctggcgaaac gctatcgctg   2700
gtgggcgagt ctgcagcggg taaatccact accgggcggg cgttgctgcg cctggtcgaa   2760
tcgcagggcg gcgaaattat ctttaacggt cagcgaatcg ataccttgtc acccggcaaa   2820
```

```
cttcaggcat tacgccggga tattcagttt atttttcagg acccttacgc ttcgctggac    2880
ccacgtcaga ccatcggtga ttcgattatc gaaccgctgc gtgtacacgg tttattgcca    2940
ggtaaagacg cggctgcacg cgttgcgtgg ttgctggagc gcgtgggcct gttacctgaa    3000
catgcctggc gttacccgca tgagttttcc ggcggtcagc gccagcgcat ctgcattgct    3060
cgcgcgttgg cattgaatcc aaaagtgatc attgccgacg aagccgtttc ggcgctggat    3120
gtttctattc gcgggcagat tatcaacttg ttgctcgatc tccagcgtga tttcggcatt    3180
gcgtatctgt ttatctccca cgatatggcg gtggtagagc ggattagtca tcgtgtggcg    3240
gtgatgtatc tcgggcaaat tgttgaaatt ggtccacggc gcgcggtctt cgaaaacccg    3300
cagcatcctt atacgcgtaa attactggcg gcagttccgg tcgctgaacc gtcccgacaa    3360
cgaccgcagc gtgtactgct gtcggacgat cttcccagca atattcatct gcgtggcgaa    3420
gaggtggcag ccgtctcgtt gcaatgcgtc gggccggggc attacgtcgc acaaccacaa    3480
tcagaatacg cattcatgcg tagataacat tcaggcggaa aataaaatgg caagagctgt    3540
acaccgtagt gggttagtgg cgctgggcat tgcgacagcg ttgatggcat cttgtgcatt    3600
cgctgccaaa gatgtggtgg tggcggtagg atcgaatttc accacgctcg atccgtatga    3660
cgcaaatgac acgttatctc aggccgtagc gaaatcgttt taccaggggc tgttcggtct    3720
ggataaagag atgaaactga aaacgtgctg gcggagagt tataccgttt ccgatgacgg    3780
cattacttac accgtgaaat tgcgggaagg cattaaattc caggatggca ccgatttcaa    3840
cgccgcggcg gtgaaagcga atctggaccg gccagcgat ccggcgaatc atcttaaacg    3900
ctataacctg tataagaata ttgctaaaac ggaagcgatc gatccgacaa cggtaaagat    3960
taccctcaaa cagccgttct cagcgtttat taatattctt gcccatccgg cgaccgcgat    4020
gatttcaccg gcagcgctgg aaaaatatgg caaggagatt ggttttatc cggtgggaac    4080 cggaccgtat gaactggata cctggaatca gaccgatttt gtgaaggtga aaaaattcgc    4140
gggttactgg cagccaggat tgcccaaact ggacagcata acctggcgtc cggtggcgga    4200
taacaacacc cgcgcggcaa tgctgcaaac cggtgaagcg cagtttgctt tccccattcc    4260
ttacgagcag gccacactgc tggagaaaaa caaaaatatc gagttgatgg ccagtccgtc    4320
aattatgcag cgttatatca gtatgaacgt gacgcaaaag ccgttcgata acccgaaggt    4380
ccgtgaggcg ctgaattacg ccattaaccg tccggcgctg gtgaaagttg cctttgcggg    4440
ctatgcaacg ccagctactg gtgtggtacc gccaagtatc gcctacgcgc aaagttataa    4500
accgtggcct tacgatccag tgaaagcgcg cgaattactg aaagaggcgg gatatcccaa    4560
cggtttcagt accacgctgt ggtcgtcaca taaccacagc accgcgcaga agtgctgca    4620 atttacccag cagcagttag cgcaggtcgg gattaaagcc caggtgactg cgatggatgc    4680
cggacagcgg gcggcagaag ttgaaggtaa agggcaaaaa gagagcggcg tgcggatgtt    4740
ctacactggc tggtcggctt caaccggcga agcggactgg gcactatcgc cgctgtttgc    4800
ctcgcagaac tggccaccga cgctgtttaa taccgcgttt tacagcaata acaggtgga    4860 tgacttcctg gctcaggcac tgaaaactaa tgatccggcg aaaagaccc gcttatataa    4920 ggcggcgcag gatatcatct ggcaagaatc gccgtggatc ccgctggtgg tagaaaaact    4980
ggtgtcggca cacagtaaaa acctgaccgg ttttggatc atgccagaca ccggcttcag    5040
ctttgaagac gcggatttgc aataagcaac gcagggagtg gaatgcttaa ttacgttatc    5100
aaacgcttac tggggttgat tccgacgctg tttatcgtct cggtgctggt gtttttattt    5160
gtccatatgc tgcccggcga tccggcgcga ttgattgccg ggcccgaagc tgatgcgcag    5220
```

```
gttatagaac tggtgcgtca gcagctgggg ttggatcagc cgctgtatca ccagttctgg   5280
cactatatca gcaatgctgt gcaggggggat tttggcctgt cgatggtgtc gcgtcgtccg   5340
gttgccgatg agattgccag ccgctttatg ccaacgctgt ggctgaccat aaccagtatg   5400
gtctgggcgg ttatatttgg tatggcggcg ggaattatcg ccgccgtctg gcgtaaccgt   5460
tggccggatc gattgagtat gaccattgcg gtgtcgggga tctcgtttcc ggcatttgct   5520
ctggggatgc ttttaattca ggtattctcc gttgaactgg gctggctgcc taccgtggga   5580
gcagacagtt ggcagcacta cattttaccc tccctgacgc tcggcgcggc agtggccgcc   5640
gtgatggcgc gctttacccg cgcgtcgttt gtcgatgttt taagcgaaga ttatatgcgt   5700
accgcgaggg cgaaaggggt gagcgaaacc tgggttgtcc tcaaacacgg gctacgtaac   5760
gcgatgatcc cggtagtgac catgatgggc ttacagtttg gcttttttgct cggtggttcc   5820 atcgttgtgg agaaagtttt caactggccg ggacttggac gcttactcgt tgactccgta   5880
gaaatgcgtg attacccggt gattcaggcg gaaattctgc ttttctcgct ggaatttatt   5940
cttatcaact tagtggtgga tgtgctttac gccgccatta acccggctat caggtacaag   6000
taaggatgcg actatttaac tggcgacgtc aggcggtgtt aaacgccatg ccactggtca   6060
aacctgacca ggtacgtaca ccgtggcatg aattctggcg acgatttcgc cgtcagcata   6120
tggcgatgac cgccgcatta ttcgttattt tattgattgt ggtggccatt tttgcacgct   6180
ggatcgctcc ctatgacgcc gaaaattatt ttgattatga caatctgaat aacggacctt   6240 cttttgcagca ctggtttggc gtcgattcac tggggcgtga cattttcagc cgtgtcctgg   6300
ttggtgcgca aatctcgctg gcggcgggcg tgtttgccgt gtttatcggt gcggcgatcg   6360
ggacgttgct gggcttgctc gctggatatt atgaaggctg gtgggatcgg ctgatcatgc   6420
gcatttgcga tgtgctgttt gccttcccgg gtatttact ggcgatcgct gttgttgcgg   6480
tgttgggaag cggcattgct aacgtgatta ttgcagtcgc cattttttcc atccccgcgt   6540
ttgcccgcct ggtgcgcggc aacacgctgg tgttgaaaca gcaaaccttt attgagtcag   6600
cacgcagtat tggtgccagc gatatgaccg ttttgttgcg tcatatcctg cctgggaccg   6660
tctcttctat cgtggtgttt ttcaccatgc gcattggtac ctcgattatc tctgccgcca   6720
gcctctcatt tctcggcctc ggtgcgcagc cgccgacacc agagtgggga gcaatgctca   6780
atgaggctcg agcggatatg gttatcgcgc cgcatgtcgc tgttttttccg gccctggcta   6840 tttttctgac cgtactggcg ttcaatttgt tgggcgatgg tttacgcgat gcgctggatc   6900
cgaaaattaa aggatagtta cgtttgaata ttgcttgaaa gggtaatcac ctcacaggaa   6960
attattgccc taagcaagtg ttgtaacttt ctgctgattt tgtagaatcg ggtaatttgg   7020
ttaaaaagcc gcagcaaggg acaattttg cagcggcaca gcgttcagat agttatttttg   7080 ttaaatgtat taacatgctg agtttatacg aaaagataaa gataaggctg ataattttat   7140
ttttattggc agcactgtca tttattggtc ttttttttcat cattaactat caactggtat   7200
cggagcgcgc ggtaaaacgt gccgatagcg gctttgaact tattcagaaa acgttggct   7260 atttctttaa agatattgaa cgttcggccc tgacattaaa ggactcactg tatttattaa   7320
aaaatacaga ggagattcaa cgcgccgtga ttcttaaaat ggaaatgatg ccattttttag   7380 actcggtggg actggtactt gatgataata aatattatct ttttcgcgg agggcgaatg   7440 ataaaatcgt tgtttatcat caggaacaag taaatggacc gcttgtcgac gagtcagggc   7500
gggttatttt tgccgatttt aacccatcga acgaccgtg tcggtggct tcagatgact   7560 ctaacaacag ctggaatccg gcatacaatt gctttgatcg tccgggtaaa aaatgtatct   7620
```

```
cttttacgct acacatcaac ggcaaagatc acgatttgtt agcggtggat aaaattcatg   7680
tcgatttaaa ctggcgatat ctgaacgagt atcttgatca aatcagcgct aatgatgaag   7740
ttctatttt gaaacaaggc catgagatca ttgccaagaa tcaactcgct cgtgaaaaac    7800
tgattattta taatagcgaa ggtaattata atattattga ttctgtcgat actgaatata   7860
tcgaaaaaac atcagcggtg ccaaacaacg cattattcga atctatttt tattatcctg    7920
gcggtaattt attgaacgca tcagataaac tttttatct gccgtttgcg ttcattatta    7980
tcgtattgct ggtggtttat ttaatgacca ctcgtgtgtt ccgtcggcaa tttcctgaaa    8040
tgacagagct ggttaatacg ctggcgtttt tgcctgactc aacggatcaa atcgaggctc   8100
tgaaaattcg tgaaggcgat gcgaagagaa ttatcagcat caaaaattcg atcgcggaaa   8160
tgaaagatgc cgaaattgaa cggtcaaata aattgctctc actgatctct tacgatcagg   8220
aaagtggttt tattaaaat atggcgatta ttgagtctaa caataatcag tatctggctg     8280
tggggatcat caaactgtgt ggtctggaag ccgtggaagc ggtgtttggt gttgatgagc   8340
gcaataaaat cgtcaggaaa ttgtgtcagc gaattgccga aaatatgcg caatgctgcg     8400
atatcgtgac attcaatgcc gatctctatt tacttctgtg tcgggaaaat gtacagacat   8460
ttacccgtaa aatagcgatg gtaaacgatt ttgacagcag ctttggctac cgcaatctgc   8520
gcatccataa gtctgccatt tgtgaacctt gcaggggga aaacgcctgg agttacgcag    8580
aaaaactgaa actggcgatt ccagtatcc gtgaccatat gttctcagag tttatttct    8640
gtgatgacgc gaaactcaac gaaatagaag agaatatctg gattgcgcgt aatattcgcc   8700
atgcaatgga aattggcgaa ctattcctcg tctatcaacc gatcgttgat attaacaccc   8760
gcgccattct gggcgcggag gcgttgtgcc gttgggtgtc tgcggagcgg gggatcattt   8820
caccgctgaa gttcattacc attgctgaag atatcgggtt tatcaatgag ctgggttatc   8880
agattattaa aacggcaatg ggtgaattca gacattttag tcagcgtgcg tcgctgaagg   8940
atgatttctt actgcatatt aatgtttcgc cctggcagtt aaacgaacca cactttcatg   9000
agcgttttac caccatcatg aaagaaaatg gcctgaaggc gaacagcctc tgtgttgaga   9060
tcactgaaac cgtgatcgag cgaattaatg aacatttta tctcaatatt gaacaactgc    9120
gtaaacaagg ggtacggata tcgattgatg actttggcac cggtttgtca aacctgaaac   9180
gttttatga aattaatcca gacagcataa aggtggactc gcaattcacc ggcgatattt    9240
tcggtactgc gggaaaaatt gtgcgcatta ttttcgacct ggcacgctat aaccggatcc   9300
cggtgattgc ggaaggcgta gagagcgaag acgttgcgcg cgaattaatc aaattaggat   9360
gtgttcaggc tcaggggtat ctgtaccaga aacccatgcc attctccgcc tgggataaaa   9420
gtggaaaatt agtaaaagag tagtttacgt atgtccagaa tcaataagtt cgtacttaca   9480
gtcagtctgc tgattttat catgatttca gcagttgcct gcgggatcta cactcaaatg    9540
gtaaaggaac gggtgtatag cctgaaacag tccgttattg atactgcttt tgcggtggca   9600
aatattgctg aatatcggcg tagcgtggca attgatctta tcaacacgct aaatcccacg   9660
gaggaacagc tgttggttgg tttgcgcaca gcttacgccg actcggttc cccctcttat    9720
ttgtacgatg tcggtcctta tctgatttcc agtgacgaat gtattcaggt aaaggagttc   9780
gagaaaaatt attgtgcaga tattatgcag gttgtgaagt atcgacatgt caaaaataca   9840
gggtttatct cttttgacgg taaaaccttc gtctattacc tctatccggt aactcacaat   9900
cgtagtctga tattttgct tggtctggag cgttttctt tactgtcaaa atcgctggcc     9960
atggacagcg agaacctgat gttctctcta tttaagaacg gtaaaccggt gaccggtgat   10020
```

-continued

```
gaatataatg ctaaaaacgc catcttcacc gtttcggaag cgatggagca cttcgcctat    10080
ttgccgaccg gattgtatgt atttgcgtat aaaaaagatg tttatttgcg ggtttgtaca    10140
ttgattattt tctttgccgc attggtggca gtgatatcgg gtgccagttg cctctatctg    10200
gtacgcagag tgattaatcg tggtattgtg gagaagaag ccatcattaa taaccatttt    10260
gaacgcgtac tggatggcgg gcttttcttt tcggctgccg atgtcaaaaa actctacagt    10320
atgtataact cggcgttcct ggacgacctg accaaagcaa tgggcagaaa atcctttgac    10380
gaagatttaa aagcgctgcc ggaaaaaggc ggttatttgt gcctgtttga cgtcgataaa    10440
ttcaaaaaca ttaacgacac cttcggtcat ttgctgggcg atgaagtgtt gatgaaagtg    10500
gtgaaaatcc ttaaatcaca gatcccggta gataaaggta aagtctaccg cttcggcggt    10560
gacgaatttg cggtgattta tacgggtgga acgctggaag agttgctatc gattctaaaa    10620
gaaatcgttc atttccaggt gggaagcatt aatttaagta ccagtatcgg tgtagcacat    10680
tcaaatgaat gtcctaccgt cgaacgcttg aaaatgctgg cggatgagcg gctgtataag    10740
agtaagaaaa acggcagggc acagattagc tggcagtaat cattattcgc aggccggaca    10800
aatgattttg cccggcctga attaattaaa cccggctacc ccacaaatcg tactcatcgg    10860
cgtgctcgac tttcacacgc aggatatcac ccggcttaac gttggtttca ccattgagat    10920
aaaccgcgcc gtcgatttcc ggtgcatctg ccatgctgcg accaatcgcg ccttcttcgt    10980
ccacttcgtc gataatcacc agaatttcac ggcccacttt ctcttgcagg cgctcggcgg    11040
aaatctgctg ctgcagctgc atgaaacggt tccagcgttc ttctttaact tcttccgaa    11100 cctggtcagg cagggcattg gcgtctgcac cttcaaccgg gctgtattta agcagccaa    11160 cgcgatccag acgcgcttct ttcaggaagt cgagtagcat ctggaaatct tcttctgtct    11220
cgccagggaa gccgacaata aaggttgagc gtagggtcag ttccgggcag atttcgcgcc    11280
actgtttgat gcgcgccagt tggcgatcta cagaacccgg acgcttcatc agtttgaaga    11340
tgcgcgggct ggcgtgctgc aacggaatgt ccagatacgg caggattttg ccttctgcca    11400
tcagtgggat gacgtcgtcc acatgcggat aagggtaaac gtagtgcaga cgtgtccaga    11460
tccccagttt cgataactgt tcgcacaggc tgaccatgct ggttttacc ggctcgccgt    11520 tgtggaagcc agtacgatgt ttaacatcaa cgccataggc ggaagtatcc tgcgagatca    11580
ccagaatctc tttaacgccc gcatctacca gacgtttcgc ttcacttaac acttcgccaa    11640
tcggacggct caccaggtcg ccgcgcatag acggaataat gcagaaggtg cagcggtgat    11700
tacagccttc agaaatttc agataggcat aatgacgcgg cgtcagtttc acaccttgtt    11760
ctggcaccag gctcaggaat gggttgtgtt tcggttttgg cacgtagtga tgaacgtgct    11820
ccagaacctg ctcatag                                                  11837
```

<210> SEQ ID NO 2
<211> LENGTH: 3073
<212> TYPE: DNA
<213> ORGANISM: Escherichia coli

<400> SEQUENCE: 2

```
ctccgtctct ataatttggg aaaattgttt ctgaatgttc ccaaaaataa tgaatgatga      60
aaactttttc aaaaaagcgg cggcgcacgg ggaggaacct cctttaactc ctcaaaacga     120
acatcagcgg tccgggctgc gcttcgcccg tcgcgtcaga ctacccccgtg cggttggcct     180 ggctggcatg ttcttaccga ttgcttcaac gctggtttca caccccgccgc cgggctggtg     240 gtggctggtg ttggtcggct gggcgttcgt ctggccgcat ttagcctggc agatagcgag     300
```

```
cagggccgtc gatccgctta gccgggaaat ttacaactta aaaaccgatg cagtattagc    360
gggaatgtgg gtaggcgtaa tgggcgtaaa cgtgctgcct tccaccgcga tgttgatgat    420
tatgtgtctg aatttgatgg gggcaggcgg cccccgtctg tttgtcgcgg gtctggtgtt    480
gatggtggtt tcctgccttg tcaccctcga gctgacgggc attaccgtgt cgttcaatag    540
tgcgccgctg gaatggtggc tctcccttcc cattattgtc atttatcctc tgctgtttgg    600
ctgggtcagc taccagacgg caaccaaact ggcggaacat aaacgcaggt tgcaggtcat    660
gagtacccgc gacggcatga cgggcgtgta aaccgacgt cattgggaaa ctatgttacg     720
caatgaattt gataactgtc ggcggcataa tcgcgatgca acgttactga ttatcgatat    780
cgaccatttc aagagcatca acgatacctg gggccatgat gtgggcgatg aagcgattgt    840
ggcgcttacc cgacagttac aaattaccct gcgcggtagc gatgtgattg gtcggtttgg    900
cggcgatgag tttgcagtaa tcatgtccgg tacgccagct gagagcgcca ttaccgccat    960
gttacgggtg catgaagggc taaatacatt acgtttgccg aatacgccac aggtaacttt   1020
acggattagt gtggggttg cgccgctgaa cccacaaatg agtcactatc gtgagtggtt     1080
gaaatcggca gatttggcgc tttacaaagc aaagaaagcc ggacgtaacc gcaccgaagt    1140
ggcggcctga cgtccggcga aagtcatcag gatttgctga gttttttctga ttttttccata 1200 cacttcgtca tcgcttcgat cactgcagca cggaagcctt tctcttccag tacgcgtacc    1260
gcttcaatgg tggtgcctcc cggtgagcag accatatctt tcagtgcccc cggatgttct    1320
cccgtttcca gcaccatttt tgcggaaccc attaccgcct gagcggcaaa tttatacgcc    1380
tgggcgcgtg gcatcccgcc cagcacggcg gcgtcggcca tcgcttcgat aaacataaat    1440
acgtaggctg gcgaagaacc gctcacaccg accaccgggt ggatcatcgg ctcagcaatt    1500
acttccgctt cgccaaagca gcggaaaata ttcagcacat cagcggtatc ttctggggtt    1560
accagcgcgt ttggcgttac ggaggtcatc ccggcattaa ccagtgcggg agtgttcggc    1620
atggcgcgga taatttccg gtcatggccc agcgcgcggg caagctggtc gagcgtgaca     1680
cctgcagcaa tagaaacgac cagagagtct ttattcaggc tggaggtgat ttcgctaagc    1740
actttaatca tgatgccagg tttaacggca gcaaaaatga tgtcggcgat ttgcgccact    1800
tcttgcgccg attctgcggc gttgatgccg aactggtcat gcagggcggc gactttatcc    1860 ggggagggg tgtataccca gatttgccct ggaagcacct gaccgctggc aatcagaccg      1920
ccgagaatgg cttttcccat attgccgcag ccaataaaac cgattttctt ttccattgcc    1980
tcactcctgc cgtgaaattc attgttttga taatcgctgg cagaagcata aacagaacta    2040
tgccggaagg caaagcgcg acacaataga ggattaccca acaaaggatg actttatgac      2100
aatttgggtg gatgccgacg cgtgtcccaa tgtaattaaa gagattttgt atcgcgcggc    2160
ggaacgtatg cagatgccgc tggtactggt agcaaaccag agtttacgcg tgccgccatc    2220
gcgatttatt cgtacgctgc gcgtcgcggc aggtttcgac gttgccgata cgaaattgt     2280 ccggcagtgt gaagcgggcg atttggtgat caccgcagat ataccttggg ctgctgaagc    2340
catcgagaaa ggcgctgcgg cgcttaatcc gcgcggcgaa cgttacacgc cagcgaccat    2400
tcgtgagcgc ctgacgatgc gcgattttat ggatacctta cgtgccagtg ggatccagac    2460
cggcggacca gatagccttt cacaacgtga ccgccaggcc tttgccgcgg agctggagaa    2520
gtggtggctg gaagtgcaac gtagtcgtgg ctaaatgtaa tttattattt acacttcatt    2580
cttgaatatt tattggtata gtaagggtg tattgagatt ttcactttaa gtggaattt      2640 ttctttacaa tcgaaattgt actagtttga tggtatgatc gctattctca tgacaccggc    2700
```

| | |
|---|---|
| tttcgccgca ttgcgaccta ttggggaaaa cccacgatga cacaacctct ttttctgatc | 2760 |
| gggcctcggg gctgtggtaa acaacggtc ggaatggccc ttgccgattc gcttaaccgt | 2820 |
| cggtttgtcg ataccgatca gtggttgcaa tcacagctca atatgacggt cgcggagatc | 2880 |
| gtcgaaaggg aagagtgggc gggatttcgc gccagagaaa cggcggcgct ggaagcggta | 2940 |
| actgcgccat ccaccgttat cgctacaggc ggcggcatta ttctgacgga atttaatcgt | 3000 |
| cacttcatgc aaaataacgg gatcgtggtt tatttgtgtg cgccagtatc agtcctggtt | 3060 |
| aaccgactgc aag | 3073 |

<210> SEQ ID NO 3
<211> LENGTH: 2959
<212> TYPE: DNA
<213> ORGANISM: Escherichia coli

<400> SEQUENCE: 3

| | |
|---|---|
| ctgcagcggc actgggatcg gctatggtcg tgccgctggc tttgaacggt tttggctggc | 60 |
| aaggcgcgtt gctcatgctg atgtgttttc ctctgctggc tcttttttta tggctgccac | 120 |
| agtggcgaag tcaacaacat gcaaatttga gtacctcgcg cgccttacat actcggggta | 180 |
| tctggcgttc accgcttgcc tggcaggtca cattgtttct tgggatcaac tcactggtct | 240 |
| attacgtgat tattgctgg cttccggcga tcctcatcag tcacggctat agcgaagcac | 300 |
| aggcgggttc actgcatggt ttgctgcaac tagccacagc agcacccggt ttgctgatcc | 360 |
| cactttttctt acatcatgtg aaagatcagc gtggtattgc agcgttcgtt gccttgatgt | 420 |
| gcgcagtggg cgcggttggg ctctgcttta tgccagcgca cgcgatcacc tggactctgc | 480 |
| ttttcggttt tggttccggc gcaacaatga tactgggggtt gacgttcatt ggtctgcggg | 540 |
| ctagttctgc gcatcaggcg gcggcactct cggggatggc acaatccgtc gggtatttgt | 600 |
| tggcagcctg tgggccgccg ctgatgggta aaatacacga tgctaacggt aactggtctg | 660 |
| taccacttat gggtgttgcc atactttcac tactgatggc gattttcgga cttttgcgccg | 720 |
| ggagagacaa agaaattcgc taatatccgg tgctatagtg acgtaacaaa tcatgcgtga | 780 |
| aagggagaac aaacacgatg aatattcagt gcaaacgcgt ttatgatccg gctgaacaga | 840 |
| gcgatggtta tcgcatactg gtcgaccgcc tctggccgcg cggtatcaaa aaaccgattt | 900 |
| tagcccttga tgagtgggat aaagaaatca cgccgtcaac ggaactgcgc aaagcctttc | 960 |
| acggcgaagt cgtcgattat gcaaccttt cgcgagcaata tcttgcagaa ctggcgcaac | 1020 |
| acgagcaaga aggaaagcgg ctggcggaca tcgccaaaaa acagccgctg accctgctct | 1080 |
| actcagcaaa aaacaccacg cagaaccatg cgctggtgct ggccgactgg ctacgtagct | 1140 |
| tgtgatttta gtacagcatc cggcggttat ttttcaccag ccggatggtc acgccgccac | 1200 |
| aatgcccatt catcaatcgt ttcaccgccc ggtaatttgc aattgttgct gaccccttgc | 1260 |
| gctgtctgca ctgaatgag cgtcccgccc ttctgctggc aatagaccga cgccggattt | 1320 |
| gccataccaa tctgcggcgg tttaggtgct tctggctgag aaggggttga acaaccagcc | 1380 |
| aggaccagca agcaaggcag aacaaaactg ataattttca tttattgatc tcacatattt | 1440 |
| atccaagatt agagtatcgc ggtatcgttt tgttttgcag cactattttt attacattca | 1500 |
| ctcaaaacat attacgtctt gtttcatctt tgttgatgat gttttatcat gcctgcaaag | 1560 |
| attaaataat cagcatttac ccgccgtatc ctggagttgt tccgtgtcag atcagattat | 1620 |
| cgcccgcgtc tcgcaatccc ttgccaaaga acagtcactg aaagtctgg tccgacagct | 1680 |
| tctggagatg ctggaaatgg tcactgatat ggaatcaacc tacctgacca agtggatgt | 1740 |

| | |
|---|---|
| cgaagcgcgc ctgcagcata ttatgtttgc ccgtaacagc cagaaaatgt acatcccgga | 1800 |
| gaattttacc gtctcgtggg attactcgtt atgcaaacgc gccattgatg aaaactgctt | 1860 |
| tttcagcgat gaagtccccg accgttgggg tgactgtatt gcggcacgca atcttggcat | 1920 |
| caccacattt ctgagcacgc caattcactt accggatgga tcattctatg gcacgctttg | 1980 |
| cgccgccagc agtgagaagc gccagtggag tgaacgcgcg gaacaggttt tacagttatt | 2040 |
| cgccggactg attgcacaat atattcaaaa agaggcactg gttgaacagc tgcgcgaagc | 2100 |
| caatgctgcg ctgattgcgc aatcgtatac cgactcgtta accgggctac cgaatcggcg | 2160 |
| ggcgattttt gaaaatctga cgacactgtt ttccctcgcc cggcatctta accataagat | 2220 |
| aatgatcgcg tttatcgatc tggataactt caaattaatc aatgatcgtt ttggtcataa | 2280 |
| tagtggcgat ctgtttctca ttcaggttgg cgagcgcctt aatacgctcc agcaaaatgg | 2340 |
| cgaagttatt ggtcgtctcg gcggtgatga gttttttagtt gtttcactaa acaacgagaa | 2400 |
| tgcggatatt tcgtcgctgc gagaacgcat tcagcagcaa atacgtggag aatatcactt | 2460 |
| aggtgatgtt gatttgtatt atcccggtgc cagtcttggc atagtagaag tcgatcctga | 2520 |
| aacaaccgat gcagacagtg ccctgcatgc tgccgatatt gcgatgtatc aggagaaaaa | 2580 |
| acacaaacag aaaacaccct ttgtcgcgca tccagcgcta cattcctgag gcgtattcac | 2640 |
| atccttttga ttggtgataa catgcgaatc ggtattattt ttccggttgt aatcttcatt | 2700 |
| acagcggtcg tattttttagc atggttttt attggcggct atgctgcccc gggagcataa | 2760 |
| agatgaaaaa aacaacgatt attatgatgg gtgtggcgat tattgtcgta ctcggcactg | 2820 |
| agctgggatg gtggtaacgt cacctctaaa aaatagcaaa ggctgcctgt gtgcagcctt | 2880 |
| tgtgcaattt aagcgttaac ttttaatctt cctgtagata aatagcacga caatcgcacc | 2940 |
| aataacggca accacgaag | 2959 |

<210> SEQ ID NO 4
<211> LENGTH: 2643
<212> TYPE: DNA
<213> ORGANISM: Escherichia coli

<400> SEQUENCE: 4

| | |
|---|---|
| ctggcgaatc tgccgttctt cggtgatatc cgagaaagtc attaccaggt tctgcagatg | 60 |
| cgcgagcacg tcataaaccg ggctgataga ggctttaatc cagatttttt caccggtgcg | 120 |
| cgtcaacagc agaaattcgt cctgatcgcg ggcggttttc catagcaact gttgtaaacg | 180 |
| aatgcggtta tcggcaggga attcaggaat gttcaggagt gtatcgggct gcataccgct | 240 |
| ggcttcgcta atgcagtaac caaacatttc ggtaaatgcg cgattgcact gcacaatatg | 300 |
| gcgttccgga tcgaggacaa tcaccggtcg gtcgagatgg tcaacggcaa taatcaattg | 360 |
| tcgggtctgt tcttttttgcg ccatttctac gctggcatcc cgtaccagcg ccaggtaata | 420 |
| aactttcccc tcggcgctca ctttcgatag cgcaaaacgg gtccagattt tactgccgtc | 480 |
| ttttttctcc agctgcagct cccgactcat cccctcaaca cgcgctttac cgccttcacg | 540 |
| gttgtgacga atgtattcag gatgcgcagg acgcaaatcc cgcggaatca gcatatcaat | 600 |
| gttattgcca atgacttctt cacgtttgta tccccagagc ttctctgcgg cggggttgaa | 660 |
| aaacatcact tcatcatttt cgttaattaa caccgcaccc atcatatttt gctcaagggc | 720 |
| ggggaaaaaa atgccatcgg cggcattatc cgcatcggtt agcttcatga ttacctctgc | 780 |
| atcctggcgc atctaaagac tggctttcca gagttcaaca cggttctac ctcgtctttt | 840 |
| ggcgatatac agagcttcat cggctatttg aatgaggcgc tcatagtcag gatgaccatt | 900 |

```
aaacatggcg gcaccgatgg aaagtgagag ggcaatatct tcgccgtttg cggcttttcag    960
tttggttttc tccacccgac tgcgaatacg ttctgcggta cgtaacgttt cgttttcaga   1020
agcttcagtc aaaacaatga taaattcatc gcccccgtag cggaaaacat aatcactact   1080
gcggacgttg tcataaaagg cctgagagac tttacgcaga atttcatcac cagtgttatg   1140
gccccacgta tcgttgatct cttttgaattt atcaacgtca ataatcagca ctgacagcgg   1200
tgtaccggtc cggttggcat gggcaatttc gcgtttgaag atagtcggta ggaaacggcg   1260
gttaagtaat ttcgtcagta catccatacc gacttcgtgg cgcgatactt cttcaaacaa   1320
ttcacgcagc aaggtaataa tttgcgatac ggtatttctt atctgtaata aaaatttcac   1380
ccgcagactt ctgttattca aatttctggt gttacgcatg gtttgattga aaataccgtc   1440
gaaatcctga atcagacggg agatatggcc tacttcggca ataccactaa aataatgtcg   1500
acctttatgg ttaaaccaca ggccaaaatc agcctggctt aaaggcaaac tactgcctaa   1560
atcagaatcc agcaggattt tatagataat atctatttcc catgaaagta ttgaggctat   1620
ttgccgttct ttttcttctt cggcgttttc cagtaacgag aagatacgat agttttcatc   1680
ttcctttgag gcactactgt cactaaaggt aaacgcgcga gtcatcactt ccatcgcgat   1740
atcaatactg ttaatcgaga atggtagac ctgaagtttt tctgcggcgg aataatccga   1800
agagaagatc accggataga ggattttttt cagcaccccga acccccatct cgacaatttc   1860
taccggaatt cctatgcggg catgcacttc cgcgacggta tgctggattt gtattagcct   1920
ttcgacatcg tcaacctggg cagaaagcac gttaataatc cagcgttcca tcgcactctt   1980
caactgccgc tcaacttgtt cattactcaa gaattcttcg gcatgcgggt cgatgcggac   2040
aattcgataa aactcgatac tcagataatg agcatgcgca acggcaattt ccgcggcttt   2100
agcacgaatg ggcggatctg cctgttcgac aagtccggtc cactcatctt tcattctttt   2160
aaaatacatc tccataattc acacccttat aaggctggga atcagacgg aatcaaaatg   2220
aaacgcaacg tgcgagatcg actaactgca ccatattctc ctgaaatatg aagatatact   2280
gaaaagaaat aagcgattta ggacagtttc aatctacgct actgttcttc agaagagtat   2340
agcccatcgt aattatttt cggtgacagc gaatatcgta tggttttca tattcataca   2400
tttttattag ggatttatgg ctgtttaact aagtgtggtt aatttgactt aagtaagcat   2460
gattattagt gggatagttt aagagggtaa caagccggtg ggtaaagcac cggcttgtta   2520
caaagtaaga atgggagttt aactgccccca gcgactttgc agatagctga ccgcttgttg   2580
agtctgcggt ttattcagat agtcctcacg gaacaagatg gtgccgctaa tttcgggcac   2640
agc                                                                 2643

<210> SEQ ID NO 5
<211> LENGTH: 1760
<212> TYPE: DNA
<213> ORGANISM: Escherichia coli

<400> SEQUENCE: 5
ttgcatggat agatttgtgt tttgctttta cgctaacagg catttttcctg cactgataac     60
gaatcgttga cacagtagca tcagtttcct caatgaatgt taaacggagc ttaaactcgg    120
ttaatcacat tttgttcgtc aataaacatg cagcgatttc ttccggtttg cttaccctca    180
tacattgccc ggtccgctct tccaatgacc acatccagag gctcttcagg aaatgcgcga    240
ctcacacctg ctgtcacggt aatgttgata tgcccttcag aatgtgtgat ggcatggtta    300
tcgactaact ggcaaattct gacacctgca cgacatgctt cttcatcatt agccgctttg    360
```

-continued

```
acaataatga taaattcttc gcccccgtag cgataaaccg tttcgtaatc acgcgtccaa      420
ctggctaagt aagttgccag ggtgcgtaat actacatcgc cgattaaatg cccgtaggta      480
tcattaacca atttaaatcg gtcaatatcc aacaacatta ataaagatt cagaggctca       540 gcgttgcgta actgatgatc aaaggattca tcaagaaccc gacgaccgg caatcccgtc      600 aaaacatcca tattgctacg gatcgtcagc aaataaattt tgtaatcggt taatgccgca      660
gtaaaagaaa gcaacccctc ctgaaaggcg tcgaaatgcg cgtcctgcca gtgattttca      720
acaatagcca gcattaattc ccgaccacag ttatgcatat gttgatgggc agaatccatt      780
agccgaacgt aaggtaattc atcgttatcg agtggcccca gatgatcaat ccaccgacca      840
aactggcaca gtccataaga atggttatcc gttatttctg gcttactggc atctctcgcg      900
accacgctgt gaaacatact caccagccac tggtagtggg catcgatagc cttattgaga      960
tttaacaaga tggcatcaat ttccgttgtc ttcttgatca ttgccactcc tttttcacag     1020
ttccttgtgc gcgctattct aacgagagaa aagcaaaatt acgtcaatat tttcatagaa     1080
atccgaagtt atgagtcatc tctgagataa cattgtgatt taaaacaaaa tcagcggata     1140
aaaaagtgtt taattctgta aattacctct gcattatcgt aaataaaagg atgacaaata     1200
gcataaccca ataccctaat ggcccagtag ttcaggccat caggctaatt tatttttatt     1260
tctgcaaatg agtgacccga acgacggccg gcgcgctttt cttatccaga ctgccactaa     1320
tgttgatcat ctggtccggc tgaacttctc gtccatcaaa gacggccgca ggaataacga     1380
cattaatttc accgctctta tcgcgaaaaa cgtaacggtc ctctcctttg tgagaaatca     1440
aattaccgcg tagtgaaacc gaagcgccat cgtgcatggt ttttgcgaaa tcaacggtca     1500
ttttttttgc atcatcggtt ccgcgatagc catcttctat tgcatgaggc ggcggtggcg     1560
ctgcatcctg ttttaaaccg ccctggtcat ctgccaacgc ataaggcatg acaagaaaac     1620
ttgctaatac aatggcctga aatttcatac taactcctta attgcgtttg gtttgactta     1680
ttaagtctgg ttgctatttt tataattgcc aaataagaat attgccaatt gttataaggc     1740
atttaaaatc agccaactag                                                 1760
```

<210> SEQ ID NO 6
<211> LENGTH: 21
<212> TYPE: DNA
<213> ORGANISM: Escherichia coli

<400> SEQUENCE: 6

```
cagtccagtt acgctggagt c                                                 21
```

<210> SEQ ID NO 7
<211> LENGTH: 24
<212> TYPE: DNA
<213> ORGANISM: Escherichia coli

<400> SEQUENCE: 7

```
ggtcaggtat gatttaaatg gtca                                              24
```

MIXED-LIBRARY PARALLEL GENE MAPPING QUANTITATIVE MICRO-ARRAY TECHNIQUE FOR GENOME-WIDE IDENTIFICATION OF TRAIT CONFERRING GENES

RELATED APPLICATIONS

The present application claims the benefit under 35 U.S.C. §119(e) of provisional U.S. patent application Ser. No. 60/611,377, filed on Sep. 20, 2004.

FEDERALLY FUNDED RESEARCH

The studies disclosed herein were supported in part by grant BES0228584 from the National Science Foundation. The U.S. government may have certain rights to practice the subject invention.

FIELD

The present invention relates to methods and compositions for identification of genetic elements that confer phenotypic traits. In certain embodiments, the methods may involve screening multiple genomic libraries of varying insert size. In particular embodiments, microarray analysis may be used to screen genomic libraries. In more particular embodiments, wavelet based multiresolution data analysis may be used to identify trait-associated or trait-conferring genetic elements.

BACKGROUND

A central goal of functional genomics is to identify genes or other genetic elements (e.g., operons) that are associated with or result in particular phenotypic traits. With the completion of the Human Genome Project and related efforts in other species, a great deal of raw genomic sequence information has become available. However, in many cases the location of expression units (genes) within this vast amount of sequence information remains to be determined. Even where genes or other genetic elements have been identified, their function is frequently unknown.

Both positive and negative phenotypic traits may be conferred by the interplay between genetic elements and environmental conditions. Positive traits may include such characteristics as growth rate, yield, disease resistance, resistance to environmental stresses such as temperature or drought, ability to grow on minimal media, etc. Examples of negative traits might include a predisposition or susceptibility to develop genetically based diseases, such as cancer, heart disease, diabetes and other conditions. In either case, it would be advantageous for the scientist, clinician or other researcher to be able to identify those genetic elements that influence or result in particular traits. Although identification of trait associated genetic elements is of significance in eukaryotes, it is also important in prokaryotes for applications such as biopharmaceutical production, bioremediation, development of chemical tolerance, identification and/or neutralization of antibiotic resistance genes, etc.

A variety of approaches have been attempted to identify trait conferring genetic elements. One approach has been to examine gene expression profiles in different tissues (e.g., diseased vs. normal), at different developmental stages, in response to various environmental factors, or across different physiological classes (e.g., DeRisi et al., 1997 *Science* 278, 680-685; Roberts et al., 2000, *Science* 287, 873-880; Schena et al., 1995, *Science* 270, 467-470). Other approaches have included transformation, gene deletion and complementation studies (see, e.g., Sambrook et al., 1989, *Molecular Cloning: A Laboratory Manual*, Cold Spring Harbor Laboratory Press, Plainview, N.Y.). Various techniques have utilized deletion libraries marked with identifiable sequences to replace individual genes, analyzed on oligonucleotides or PCR-based spotted microarrays (Winzeler et al., 1999, *Science* 285, 901-906; Shoemaker et al., 1996, *Nat. Genet.* 14, 450-456; Badarinarayana et al., 2001, *Nat. Biotechnol.* 19, 1060-1064). Other alternatives have included overexpression libraries studied by standard plating methodologies (Cho et al., 1998, *Proc. Natl. Acad. Sci. USA* 95, 3752-3757). More recently, a genome-wide screening technique using hybridization to DNA microarrays has been attempted (Gill et al., 2002, *Proc. Natl. Acad. Sci. USA* 99:7033-38). Even though DNA microarrays have been used to probe extra-chromosomally based genomic libraries in *E. coli*, such approaches have been severely limited by a requirement for substantial subcloning of regions of selected chromosomal DNA and, as a consequence, they do not provide quantitative data concerning the effect of overexpression or increased copy on a relevant phenotype.

Despite these efforts, the identification of genes conferring particular traits of interest has lagged significantly behind genome sequencing efforts. One problem with such approaches has been in the identification of a trait conferring gene within inserts containing multiple genes or genetic elements. Another difficulty has been in the detection of trait causing genetic elements against a considerable background of genetic "noise," such as random or unexplained differences in gene expression levels or allele frequencies that are unrelated to the trait of interest. A lack of reproducibility in trait associated gene mapping studies has generally resulted. An unresolved need exists for reliable and reproducible methods and compositions capable of identifying trait associated and/or trait conferring genetic elements.

SUMMARY

The present invention fulfills an unresolved need by providing methods and compositions for the genome wide identification of trait conferring genes. A preferred embodiment concerns a Multi-Library Parallel Gene Trait Mapping (ML-PGTM) method. In various embodiments, that technique may involve the simultaneous screening of several different plasmid libraries of defined insert sizes, followed by micro-array and/or mathematical analyses. The ML-PGTM method is of use to quantitatively pinpoint one or more genetic elements conferring or associated with a trait of interest. The method may be used to effectively sequence thousands of inserts and identify those clones and/or subclones which contain a genetic element that confers a trait. The analysis may also be used to determine the selective advantage of each subclone or clone in a population, giving valuable information regarding a gene's function. For example if one subclone, identifying a single gene (e.g. an enzyme) is sufficient for a trait, yet a larger clone including a transporter provides further amplification of the same trait, hypotheses may be generated and tested regarding the mechanism(s) by which those gene(s) act to confer a trait.

Various embodiments concern compositions comprising isolated nucleic acids. The nucleic acids may comprise sequences of one or more genetic elements that confer a trait. In exemplary embodiments, the nucleic acids may confer the trait of growth rate enhancement in prokaryotes. In particular embodiments, the isolated nucleic acids may comprise any part or all of the sequences disclosed in SEQ ID NO: 1-6.

Those sequences correspond to nucleotides 865,108 to 876,944 (YliF, SEQ ID NO:1); 402,893 to 405,965 (adrA, SEQ ID NO:2); 1,874,136 to 1,877,094 (yeaP, SEQ ID NO:3); 1,562,990 to 1,565,632 (yddV, SEQ ID NO:4); 1,620,874 to 1,622,633 (ydeH, SEQ ID NO:5) of the *E. coli* K12 genomic sequence (GenBank Accession No. NC_000913, ATCC Deposit No. 29425). The isolated nucleic acids may be single stranded, double stranded and/or triple stranded.

Other embodiments concern vectors comprising isolated nucleic acids as discussed above. Any type of vector known in the art may be used. The vectors may be expression vectors, with one or more promoters operably linked to the isolated nucleic acids. Vectors that may be of use in the claimed methods and compositions may include, for example, any of those disclosed in U.S. Provisional Patent Application Ser. No. 60/708,177, entitled "Broad Host Range Vectors for Shotgun and Expression Library Cloning in Gram Negative Bacteria," filed Aug. 15, 2005, the entire text of which is incorporated herein by reference. Other exemplary vectors of use may include plasmid, cosmid, BAC, YAC, bacteriophage, viral, retroviral or any other known vectors. Non-limiting examples of particular vectors of use include the pSMART™ LCKan plasmid (Lucigen, Middleton, Wis.) and the pEZSeq vector (Lucigen Corp., Middleton, Wis.).

Still other embodiments concern transformed bacteria comprising a vector as discussed above. In preferred embodiments, the bacteria is a Gram negative bacteria. In more preferred embodiments, the bacteria is a strain of *E. coli*, such as *E. coli* K12. In an exemplary embodiment, the bacteria may be the MACH1™-T1® (Invitrogen) strain of *E. coli*. A wide variety of techniques for bacterial transformation are known in the art and any such known technique may be used, including but not limited to protoplast fusion, electroporation, bacteriophage mediated transformation, liposomal uptake, etc. Exemplary methods for protoplast fusion based transformation methods are disclosed in U.S. Provisional Patent Application Ser. No. 60/701,242, entitled, "Method for efficient generation, fusion and recovery of protoplasts of Gram negative bacteria," filed Jul. 21, 2005, the entire text of which is incorporated herein by reference. In various embodiments, the isolated nucleic acid and/or vector may become chromosomally incorporated or may be extrachromosomal (episomal).

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

FIG. 8 Growth Rates for genomic segments. Maximal growth rates were calculated form growth curves performed in 96 well format.

DESCRIPTION OF ILLUSTRATIVE EMBODIMENTS

Definitions

Terms that are not otherwise defined herein are used in accordance with their plain and ordinary meaning.

As used herein, "a" or "an" may mean one or more than one of an item.

As used herein "operably linked" and "operably coupled" refer to a functional linkage between a promoter and/or other regulatory element and a second nucleic acid sequence, wherein the promoter initiates and mediates transcription of the second sequence.

As used herein, a "genetic element" includes genes, gene products (such as RNA molecules and polypeptides), assemblages of more than one gene (e.g., operons), cis-acting regulatory elements (e.g., promoters, enhancers, transcription factor binding sites) and/or transacting regulatory elements. Any sequence or assemblage of nucleic acids that may affect the phenotype of a cell containing the sequence or assemblage may constitute a "genetic element".

A genetic element may be said to "confer" a trait when the genetic element, alone or in combination with other genetic elements, when introduced into a host bacterial cell line is sufficient to either provide that trait to a bacterial cell line that did not exhibit the trait in its native (non-transformed) state, or to increase the expression of the trait over its baseline level in the native state. A genetic element may be said to be "associated" with a trait when the removal or inhibition of the genetic element in a bacterial cell line results in an increased or decreased level of expression of the trait, or when the addition of the genetic element to a bacterial cell line results in an increased or decreased level of expression of the trait. Generally, a genetic element that "confers" a trait would be expected to have a direct effect on the trait, while a genetic element "associated" with a trait might be expected to act indirectly upon other genetic elements that "confer" the trait.

Mixed-Library Parallel Gene Trait Mapping

The Mixed-Library Parallel Gene Trait Mapping (ML-PGTM) method disclosed herein may be used to simultaneously map the effect of thousands of genes on a desired trait or phenotype. In certain embodiments, the method involves selection of a mixture of plasmid based genomic libraries of varying insert sizes. Micro-array analysis of enriched plasmid DNA, along with a wavelet based multiresolution analysis precisely identifies the relevant genetic elements.

This technique allows for the identification of single open reading frames as well as larger fragments, such as operons, that confer or amplify a given phenotype. In one exemplary embodiment of the ML-PGTM method, $E.$ $Coli$ transformants were selected for increased growth rate in minimal media using genomic libraries with 0.5 kb, 1 kb, 2 kb, 4 kb and 8 kb insert sizes.

Figure 1:
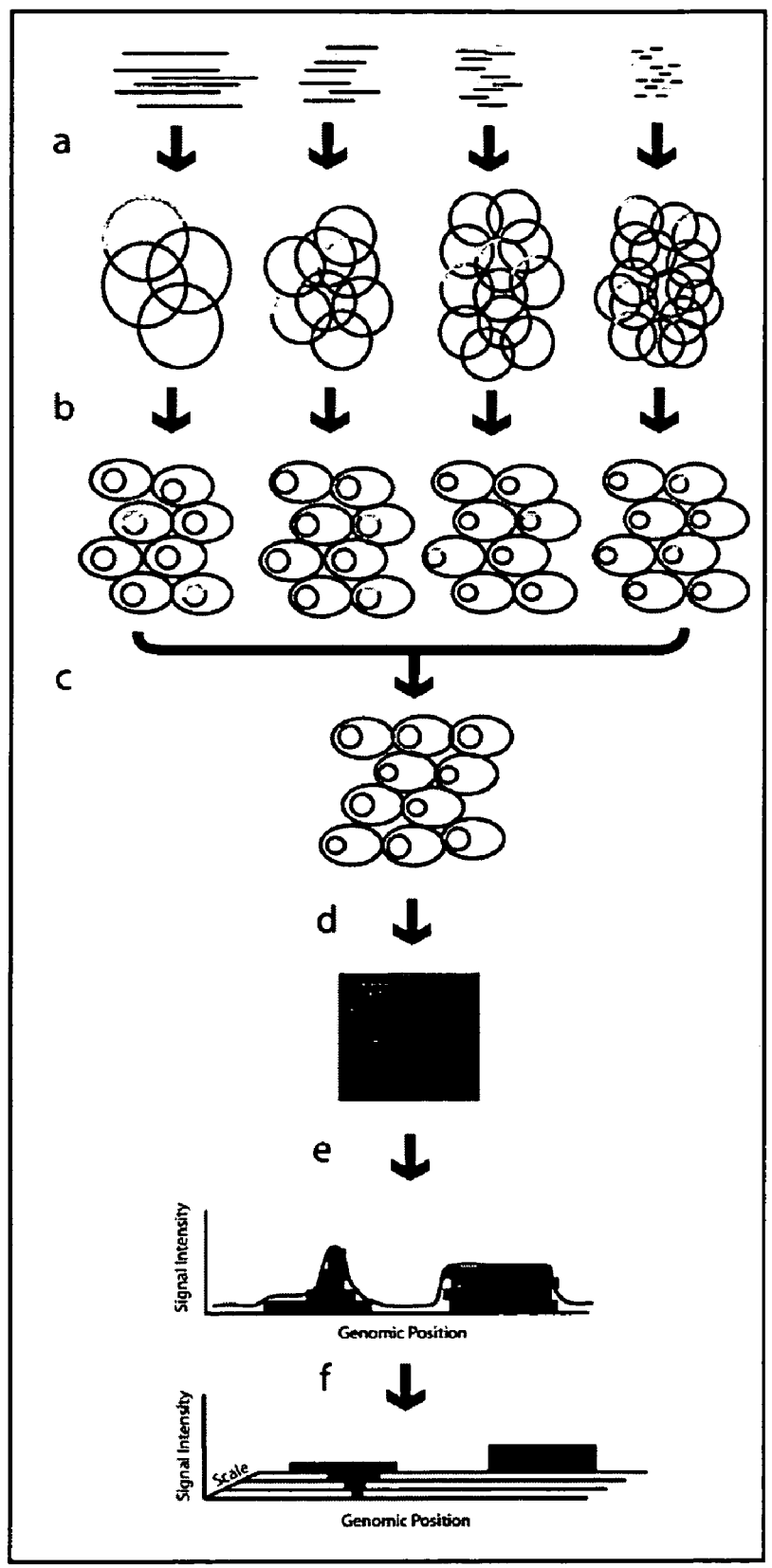
FIG. 1 shows an exemplary overview of Mixed Library Parallel Gene Trait Mapping. a) Genomic DNA fragmented to several specific sizes is ligated into vectors creating several libraries with defined insert sizes. b) These libraries are individually transformed into the cell line used for selections. c) The pools of transformants are mixed and subjected to selection. Only clones bearing plasmids with inserts increasing fitness survive. d) Plasmids are purified from the selected population, prepared for hybridization and applied to a micro-array. e) After analyzing the micro-array signal, the signal is plotted as a function of sequence position. f) A multiresolution analysis utilizing wavelets gives the signal not only as a function of position but also of scale or library size. This data can be used to pinpoint the genetic elements of interest.

An overview of ML-PGTM is depicted in FIG. 1. Briefly, several plasmid libraries are constructed with the DNA to be screened. The libraries are of defined insert sizes. In the non-limiting Example disclosed below, inserts were increased by multiples of two for simplified subsequent mathematical analyses. These libraries are individually transformed into the cell line to be screened. Transformed populations are mixed and subjected to selection for a desired trait, in one exemplary embodiment the trait of enhanced growth rate. Enriched plasmids are purified from the selected population, labeled and hybridized to a DNA micro-array. Micro-array probe level signals are plotted as a function of genome position. This signal is then subjected to a wavelet based multiresolution analysis, which decomposes the signal into scales or the signal contribution from each of the defined sized libraries.

Selections performed on such mixed libraries would produce unique signal intensity patterns along the genome that would indicate specific combinations of genes or regions required for altered growth. That is, for phenotypes resulting from the overexpression of short pieces of genomic DNA (i.e., a single gene, sRNA or perhaps DNA binding motif), enrichment of the insert DNA would occur in each of the libraries constructed and result in a sharp signal intensity peak corresponding to the gene of interest. In contrast, for those phenotypes dependent upon the overexpression of a larger region of genomic DNA (i.e. an operon), enrichment would occur only in those libraries containing the largest insert DNA leading to a broad signal intensity peak corresponding to the relevant genes.

As disclosed in the Examples below, using this approach, we have measured genome-wide, quantitative growth data for $E.$ $coli$ and have identified several genomic regions for which increased copy improves growth rate in minimal media by 50% when compared to an empty plasmid control. Micro-arrays and their subsequent analysis identified several smaller genetic elements as well as larger ones to be responsible for the increased growth rate. These results were subsequently confirmed by individual growth experiments. In addition to identifying genes resulting in large increases in growth rate, a detailed analysis is capable of calculating growth rates associated with each scale and position across the entire genome, providing true genome wide trait mapping. this approach is widely applicable for studying increased copy or mutation affects in other organisms. Furthermore, this approach may be combined with microarray enabled insertional mutagenesis approaches to enable comprehensive and rapid studies of the effect of duplication, mutation and/or disruption on cellular phenotypes.

Data Analysis

In various embodiments, the data analysis used in the ML-PGTM method provides a genome-wide, quantitative identification of genetic elements conferring or associated with a trait. The following discussion provides one non-limiting example of how data analysis may be performed in the ML-PGTM method.

Microarray Signal Extraction

Affymetrix $E.$ $Coli$ Antisense Gene Chip arrays (Affymetrix) were hybridized with genomic libraries containing different inserts of defined length and scanned according to the $E.$ $Coli$ expression protocol from Affymetrix, producing affymetrix.cel files. Raw chip signals were extracted from the Affymetrix files. Probe signals were extracted and grouped by affinity. These groupings were based on the predicted probe affinities suggested by Magnasco & Naef, (2003, Phys Rev E Stat Nonlin Soft Matter Phys. 68(1 Pt 1)).

The background for each probe was subtracted by a MAS 5.0 type algorithm, where the weighted average of the lowest 2% of signals from 16 chip sections were used as a measure of background.

The perfect match signal was robustly regressed against the PM-MM signals for each group. The intercept of this regression served as a measure of nonspecific signal for the probes in this group. This signal was subtracted from each probe.

Chips were normalized using a set of 5 positive control probe plasmids. These control concentrations were applied equally to each array in a range from 0 pM to 0.5 pM. Normalization was done by fitting signal intensity to a logarithmic function of the positive control probe concentration. These fit curves were used to estimate concentrations from each array for all probe signals.

Multiresolution Analysis

A Wavelet based multiresolution analysis was applied to the corrected probe signals from each chip. This was done using a modified Haar Scaling function. Rather than a direct averaging, a Tukey biweight was applied to achieve more robust estimates. The signal attributable to a given scale at a given position was calculated as the tukey biweight estimate of all probes within a half a scales distance in either direction from the position in question. This was done for 8000 bp, 4000 bp, 2000 bp, 1000 bp and 500 bp scales, if the density of probes in a given region permitted all scales to be calculated. At any position the scale signals were normalized such that their sum was equal to the original signal at that position. This original signal was estimated by the signal of the smallest scale available.

Growth rates for a given scale centered at a given position were calculated using a standard Monod equation, substituting the scale signals as estimations of concentrations.

Micro-Arrays

In particular embodiments, the methods disclosed herein may utilize one or more microarray devices for analysis of genetic elements. It is contemplated that any type of microarray known in the art may be used. A variety of nucleic acid microarrays are known and/or are commercially available. For example, $E.$ $Coli$ Antisense Gene Chip arrays (Affymetrix, Santa Clara, Calif.), may be of use in specific embodiments. Generally, microarrays will comprise ordered arrays of nucleic acids, such as nucleic acid probes, that are covalently or non-covalently attached to a chip surface (e.g., Schena, ed., "DNA Microarrays A Practical Approach," Oxoford University Press; Marshall et al. (1998) Nat. Biotechnol. 16:27-31; each incorporated herein by reference).

Nucleic Acids

In various embodiments, isolated nucleic acids may encode proteins that confer or are associated with a trait. In other embodiments, the nucleic acid itself may confer or be associated with a trait. The isolated nucleic acid may be derived from genomic DNA, complementary DNA (cDNA) or synthetic DNA.

A "nucleic acid" includes single-stranded and double-stranded molecules, as well as DNA, RNA, chemically modified nucleic acids and nucleic acid analogs. It is contemplated that a nucleic acid may be of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater nucleotide residues in length, up to a full length protein encoding or regulatory genetic element. In some cases, nucleic acids may comprise one or more genes.

In certain embodiments, proteins and/or peptides of interest may be encoded by any nucleic acid sequence that encodes the appropriate sequence of amino acids. The skilled artisan is aware that alternative nucleic acid sequences may be used to encode the same trait-conferring protein. In various embodiments, native nucleic acid sequences encoding selected proteins or peptides may be used in the claimed methods and compositions. In alternative embodiments, synthetic nucleic acids encoding the same or a similar amino acid sequence may be used. The design and production of nucleic acids encoding a desired amino acid sequence is well known to those of skill in the art, using standardized codon tables well known in the art. The codons selected for encoding each amino acid may be modified to optimize expression of the nucleic acid in the host cell of interest, for example by using codons optimized for expression in Gram negative or other types of bacteria. Codon preferences for various species of host cell are well known in the art.

Construction of Nucleic Acids

Isolated nucleic acids may be made by any method known in the art, for example using standard recombinant methods, synthetic techniques, or combinations thereof. In some embodiments, the nucleic acids may be cloned, amplified, or otherwise constructed.

The nucleic acids may conveniently comprise sequences in addition to a trait conferring or trait associated genetic element. For example, a multi-cloning site comprising one or more endonuclease restriction sites may be added. Regulatory sequences may be added to promote expression of the nucleic acid. A nucleic acid may be attached to a vector, adapter, or linker for cloning and/or expression of a nucleic acid. Additional sequences may be added to such cloning and/or expression sequences to optimize their function in cloning and/or expression, to aid in isolation of the nucleic acid, or to improve the introduction of the nucleic acid into a cell. Use of cloning vectors, expression vectors, adapters, and linkers is well known in the art.

Recombinant Methods for Constructing Nucleic Acids

Isolated nucleic acids may be obtained from bacterial or other sources using any number of cloning methodologies known in the art. In some embodiments, oligonucleotide probes which selectively hybridize, under stringent conditions, to the nucleic acids are used to identify a sequence in a genomic DNA library. Methods for construction of genomic libraries are known and any such known methods may be used. [See, e.g., Current Protocols in Molecular Biology, Ausubel, et al., Eds., Greene Publishing and Wiley-Interscience, New York (1995); Sambrook, et al., Molecular Cloning: A Laboratory Manual, 2nd Ed., Cold Spring Harbor Laboratory Vols. 1-3 (1989); Methods in Enzymology, Vol. 152, Guide to Molecular Cloning Techniques, Berger and Kimmel, Eds., San Diego: Academic Press, Inc. (1987).]

Nucleic Acid Screening and Isolation

Genomic libraries, transgenic or native bacteria may be screened for the presence and/or expression levels of an identified genetic element of interest using a probe based upon one or more sequences, such as those disclosed in SEQ ID NO:1-5. Various degrees of stringency of hybridization may be employed in the assay. As the conditions for hybridization become more stringent, there must be a greater degree of complementarity between the probe and the target for duplex formation to occur. The degree of stringency may be controlled by temperature, ionic strength, pH and/or the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, minor sequence variations in the probes and primers may be compensated for by reducing the stringency of the hybridization and/or wash medium.

High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleotide content of the target sequence(s), the charge composition of the nucleic acid(s), and to the presence or concentration of formamide, tetramethylammonium chloride or other solvent(s) in a hybridization mixture. Nucleic acids may be completely complementary to a target sequence or may exhibit one or more mismatches.

Nucleic Acid Amplification

Nucleic acids of interest may also be amplified using a variety of known amplification techniques. For instance, polymerase chain reaction (PCR) technology may be used to amplify target sequences directly from genomic DNA or vector insert sequences. PCR and other in vitro amplification methods may also be useful, for example, to clone nucleic acid sequences that code for proteins to be expressed, to make nucleic acids to use as probes for detecting the presence of a target nucleic acid in samples, for nucleic acid sequencing, or for other purposes. Examples of techniques of use for nucleic acid amplification are found in Berger, Sambrook, and Ausubel, as well as Mullis et al., U.S. Pat. No. 4,683,202 (1987); and, PCR Protocols A Guide to Methods and Applications, Innis et al., Eds., Academic Press Inc., San Diego, Calif. (1990). PCR-based screening methods have been disclosed. [See, e.g., Wilfinger et al. BioTechniques, 22(3): 481-486 (1997).]

Synthetic Methods for Constructing Nucleic Acids

Isolated nucleic acids may be prepared by direct chemical synthesis by methods such as the phosphotriester method of Narang et al., Meth. Enzymol. 68:90-99 (1979); the phosphodiester method of Brown et al., Meth. Enzymol. 68:109-151 (1979); the diethylphosphoramidite method of Beaucage et al., Tetra. Lett. 22:859-1862 (1981); the solid phase phosphoramidite triester method of Beaucage and Caruthers, Tetra. Letts. 22(20): 1859-1862 (1981), using an automated synthesizer as in Needham-VanDevanter et al., Nucleic Acids Res., 12:6159-6168 (1984); or by the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. While chemical synthesis of DNA is best employed for sequences of about 100 bases or less, longer sequences may be obtained by the ligation of shorter sequences.

Covalent Modification of Nucleic Acids

A variety of cross-linking agents, alkylating agents and radical generating species may be used to bind, label, detect, and/or cleave nucleic acids. For example, Vlassov, V. V., et al., Nucleic Acids Res (1986) 14:4065-4076, disclose covalent bonding of a single-stranded DNA fragment with alkylating derivatives of nucleotides complementary to target sequences. A report of similar work by the same group is that by Knorre, D. G., et al., Biochimie (1985) 67:785-789. Iverson and Dervan also showed sequence-specific cleavage of single-stranded DNA mediated by incorporation of a modified nucleotide which was capable of activating cleavage (J Am Chem Soc (1987) 109:1241-1243). Meyer, R. B., et al., J Am Chem Soc (1989) 111:8517-8519 disclose covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., Biochemistry (1988) 27:3197-3203. Use of crosslinking in triple-helix forming probes was also disclosed by Home, et al., J Am Chem Soc (1990) 112:2435-2437. Use of N4, N4-ethanocytosine as an alkylating agent to crosslink to single-stranded oligonucleotides has also been disclosed by Webb and Matteucci, J Am Chem Soc (1986) 108:2764-2765; Nucleic Acids Res (1986) 14:7661-7674; Feteritz et al., J. Am. Chem. Soc. 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Expression Vectors

Various embodiments concern vectors comprising trait conferring nucleic acids, which vectors may be transformed into a target host cell. An expression vector will typically comprise a nucleic acid operably linked to transcriptional regulatory elements which will direct the transcription of the nucleic acid. For example, expression vectors may include a cloned growth enhancing or other trait conferring genetic element under the transcriptional control of 5' and/or 3' regulatory sequences. Expression vectors may contain a promoter sequence (e.g., one conferring inducible or constitutive, environmentally- or developmentally-regulated expression), a ribosome binding site, a start codon, a transcription termination site, and/or an origin of replication.

The vector comprising a nucleic acid will typically comprise a marker gene that confers a selectable phenotype on transformed cells. Usually, the selectable marker gene will encode antibiotic resistance, with suitable genes including genes coding for resistance to antibiotics such as beta-lactamase (penicillin resistance), streptomycin resistance, kanamycin resistance, or other such genes known in the art. Methods for selecting transformed cells using marker genes and selective agents are known in the art. Alternatively, screenable marker genes such as GUS or beta-galactosidase may be used.

EXAMPLES

The following examples are included to illustrate various embodiments of the invention. It should be appreciated by those of skill in the art that the techniques disclosed in the examples which follow represent techniques discovered to function well in the practice of the claimed methods. However, those of skill in the art should, in light of the present disclosure, appreciate that many changes may be made in the specific embodiments which are disclosed and still obtain a like or similar result without departing from the spirit and scope of the invention.

Example 1

Mixed Library Parallel Gene Trait Mapping

Methods and Materials

Bacteria, Plasmids, and Media

Wild-type *Escherichia coli* K12 (ATCC #29425) was used for the preparation of genomic DNA. Genomic libraries were constructed using the pSMART™ LCKan plasmid (Lucigen, Middleton, Wis.). Cultures for library construction were cultivated in Luria-Bertani (LB) media at 37° C. Continuous chemostat cultures were carried out with MOPS Minimal Medium (Neidehardt 1974). Antibiotic concentrations used were 20 μg kanamycin/ml, 100 μg chloramphenicol/ml.

Genomic Library Construction

Overnight cultures of the *E. coli* strain K12 were cultivated in 150 ml of LB at 37° C. to an optical density of 1.0 measured by absorbance at 600 nm. The culture was centrifuged at 5000 rpm, 4° C. for 15 min. The cell pellet was then washed in 50 ml of TES buffer: 10 mM Tris HCl, 1 mM EDTA 1.5% w/v NaCl, pH=8.0 and again centrifuged. The pellet was again resuspended in 50 ml of TES buffer. 300 μl of 20 mg/ml proteinase K (Fisher) and 3 ml of 10% w/v SDS were added to the cell suspension which was then incubated at 55° C. for 16 hours. The genomic DNA was then extracted twice with equal volumes of TE (10 mM Tris HCl, 1 mM EDTA, pH=8.0) saturated phenol followed by two extractions with TE saturated phenol/chloroform/isoamyl alcohol (25:24:1). Genomic DNA was then precipitated with $\frac{1}{10}$ volume 3 M NaOAc pH=5.5 and 0.6 volumes of isopropanol. DNA pellets were washed with 70% ethanol and resuspended in TE buffer pH=8.0.

Six samples of 50 ng of purified genomic DNA were digested with two blunt cutters AluI and RsaI (Invitrogen) both having a four base pair long recognition sequence. 50 μl reactions with four units of each enzyme plus 50 mM Tris-HCl (pH 8.0), and 10 mM $MgCl_2$ were carried out for 10, 20 30, 40, 50, and 60 minutes respectively, at 37° C. The reactions were heat inactivated at 70° C. for 15 minutes. Restriction digestions were mixed and the fragmented DNA was separated based on size using agarose gel electrophoresis.

DNA fragments of 0.5, 1, 2, 4, and greater than 8 kb were excised from the gel and purified with a Gel Extraction Kit (Qiagen), according to manufacturer's instructions. The purity of the DNA fragments was quantified using UV absorbance each with an $A_{260}/A_{280}$ absorbance ratio of >1.7.

Ligation of the purified, fragmented DNA with the pSMART™ LCKan vector was performed according to manufacturer's instructions (Lucigen, Middleton, Wis.). The ligation product was then electroporated into E. Cloni 10 G Supreme Electrocompetent Cells (Lucigen) and plated on LB+kanamycin. Dilution cultures were inoculated with 1/1000 volume of the original transformations and plated on LB+Kan in order to determine transformation efficiency and transformant numbers Three of these dilutions were plated, in order to get average transformant counts. Plates were incubated overnight at 37° C. for 24 hours.

Colonies were harvested by gently scraping the plates into TB media and incubating at 37° C. for 1 hour. Plasmids were then amplified by adding chloramphenicol to the culture and incubating at 37° C. for 30 minutes before centrifugation at 5000 rpm for 15 minutes. The plasmid DNA was extracted according to manufacturer's instructions using a HiSpeed Plasmid Midi Kit (Qiagen).

In order to confirm insert sizes and transformant numbers, overnight cultures of clones for each library were inoculated with colonies picked from the dilution plates. Plasmids were purified using a Qiaprep Spin MiniPrep Kit from Qiagen. The plasmid DNA was then digested with EcoR1. Inspection by electrophoresis showed that greater than 80% of the colonies contained an insert of the expected size.

Colony PCR using the SL1 (5'-CAG TCC AGT TAC GCT GGA GTC-3') (SEQ ID NO:6) and SR2 (5'-GGT CAG GTA TGA TTT AAA TGG TCA GT-3') (SEQ ID NO:7) primers was performed on ten colonies from the 0.5, 1, and 2 kb libraries. PCR confirmed that the colonies contained an insert of the expected size and that chimeras were not present.

Continuous Chemostat Cultures

A continuous culture system was developed with a working volume of 100 ml. MOPS minimal media plus kanamycin was introduced at a controlled volumetric flow rate by use of a peristaltic pump. Similarly, volume was maintained by an outlet pump set to a maximal flow rate at a given depth in the culture vessel. The chemostat conditions were as follows: Agitation was vigorous using a stir plate on the highest setting. Cultures were incubated at 37° C. Filtered house air was introduced for proper aeration through a sparge port. Clones exhibiting an increase in specific growth rate were selected for by increasing dilution rate gradually along the duration of the continuous culture over 100 generations.

Chemostat cultures were performed in duplicate. For each chemostat culture greater than $10^7$ clones were obtained after the transformation of these libraries into MACH1-T1 cells, once again providing adequate representation of the genome at each scale. All transformants were mixed and inoculated into chemostats containing MOPS minimal media. Cell density was monitored in the culture as the dilution rate was systematically increased.

Transformation of Library DNA

Purified plasmid DNA from each library was introduced into MACH1™-T1® (Invitrogen) by electroporation. MACH1™-T1® cultures were made electrocompetent by standard glycerol washes on ice to a final concentration of 10 cells/ml. (Molecular Cloning). Dilution cultures were inoculated with 1/1000 volume of the original transformations and plated on LB+Kan in order to determine transformation efficiency and transformant numbers. The original cultures were combined and diluted to 100 ml with MOPS Minimal Media and incubated at 37 C for 6 hours or until reaching an $OD_{600}$ of 0.50. This mixture was then introduced into a chemostat vessel and the initial dilution rate was set to 0.015 $min^{-1}$. The $OD_{600}$ of the culture was recorded every six hours and the dilution rate was adjusted according to the growth.

Sampling

Every 12 hours 100 ml of LB+kan was inoculated with a 100 µl sample collected from the outlet stream. 10 µl of the culture were plated on LB+Kan to obtain colonies for sequencing and further growth studies. The remainder was incubated at 37° C. for 12 hours, with shaking at 225 rpm. Plasmids from these cultures were amplified with chloramphenicol at 37° C. for 30 minutes before centrifugation at 5000 rpm for 15 minutes. The plasmid DNA was extracted using a HiSpeed Plasmid Midi Kit from (Qiagen) and prepared for micro-array hybridization.

Micro-Arrays

For each array, 7.5 µg of sample plasmid DNA was mixed with the following control plasmid DNA, which was similarly purified: 1000 ng pGIBS-DAP (ATCC# 87486), 100 ng pGIBS-THR (ATCC# 87484), 10 ng pGIBS-TRP (ATCC# 87485) and 1 ng pGIBS-PHE (ATCC# 87483). The plasmid mixture was digested at 37° C. overnight with 10 units each of AluI and RsaI (Invitrogen) in a reaction containing 50 mM Tris-HCl (pH 8.0), and 10 mM $MgCl_2$. Reactions were heat inactivated at 70° C. for 15 minutes. 10× One Phor All Buffer (Amersham) was added to the digestions to a final IX concentration. In addition, 2 units of RQDNAse I (Fisher) and 200 units of Exonuclease III (Fisher) were added. These reactions were carried out at 37° C. for 30 minutes followed by heat inactivation at 98° C. for 20 minutes. The fragmented single stranded DNA was then labeled with biotinylated ddUTP using the Enzo Bioarray Terminal Labeling Kit (ENZO) following the manufacturers' protocol.

Affymetrix *E. Coli* Antisense Gene Chip arrays (Affymetrix) were handled and scanned according to the *E. Coli* expression protocol from Affymetrix producing affymetrix .cel files.

Data Analysis

Probe level signals were extracted from the cel files using the Expression Exporter software (Affymetrix). For each array, in order to subtract background signal as well as any signal from genomic DNA contamination, the largest signal from any pGIBS-LYS (ATCC# 87482) probe was subtracted from all probes. This control DNA was not added to the sample and the LYS gene itself is on the chromosome of MACH 1-T1, an *E. Coli* strain W derivative. Next, outlier probes were identified and removed using the Hampel identifier, with probes signals averaged over a 250 bp range to calculate median values. Average signals of positive control probes were fit to a logarithmic function of moles. This was used to calculate the moles due to each signal in the sample. These signals were then mapped to genomic position giving a signal as a function of position. Data was padded by filling genomic positions between probes with a line connecting closest probe pairs. The resulting signal was subjected to a continuous wavelet transform to perform the multiresolution analysis. Every 10 base pairs was given a signal. This signal was subjected to a discrete wavelet transform using a Debauchies mother wavelet and WaveLab v. 8.02 Software (Rice University). The signal was reconstructed after deletion of scales smaller than 500 bp. The resulting denoised signal was subjected to a multiresolution analysis using the same software.

Growth Curves

Growth curves, were obtained with replicates using a PowerWave XS KC4 v3.1 (Biotek, Winooski, Vt.) using the kinetic mode (37° C., shaking intensity-medium) with readings taken every 30 minutes. A 1% v/v of overnight culture was used to inoculate 200 µl of MOPs minimal media plus 20 µg/ml kanamycin, in a flat bottom 96 well plate (Costar model 3370). Optical density measurements were recorded at 977 nm, 900 nm, and 600 nm, and then adjusted according to the manufacturers instructions (adjusted 600=600/((977−900)/0.18)). The adjusted 600 nm reading was used for construction of growth curves. Maximal growth rates were calculated from these curves. Growth rate was calculated as the maximal slope comprising at least 4 time points (2 hours).

Results

Four *E. Coli* K12 genomic libraries were created in the pSmart-LCKan vector. These libraries consisted of greater than $10^6$ clones with correct insert size in the case of the 0.5 kb, 1 kb, 2 kb and 4 kb libraries, and greater than $10^5$ clones with the correct insert size for the 8 kb library. In each case there is a greater than 99.9% probability that the entire genome is represented. The number of colonies required for a representational library (>99.9% of genome expressed) is dependant on the size of the insert DNA.

Figure 2:
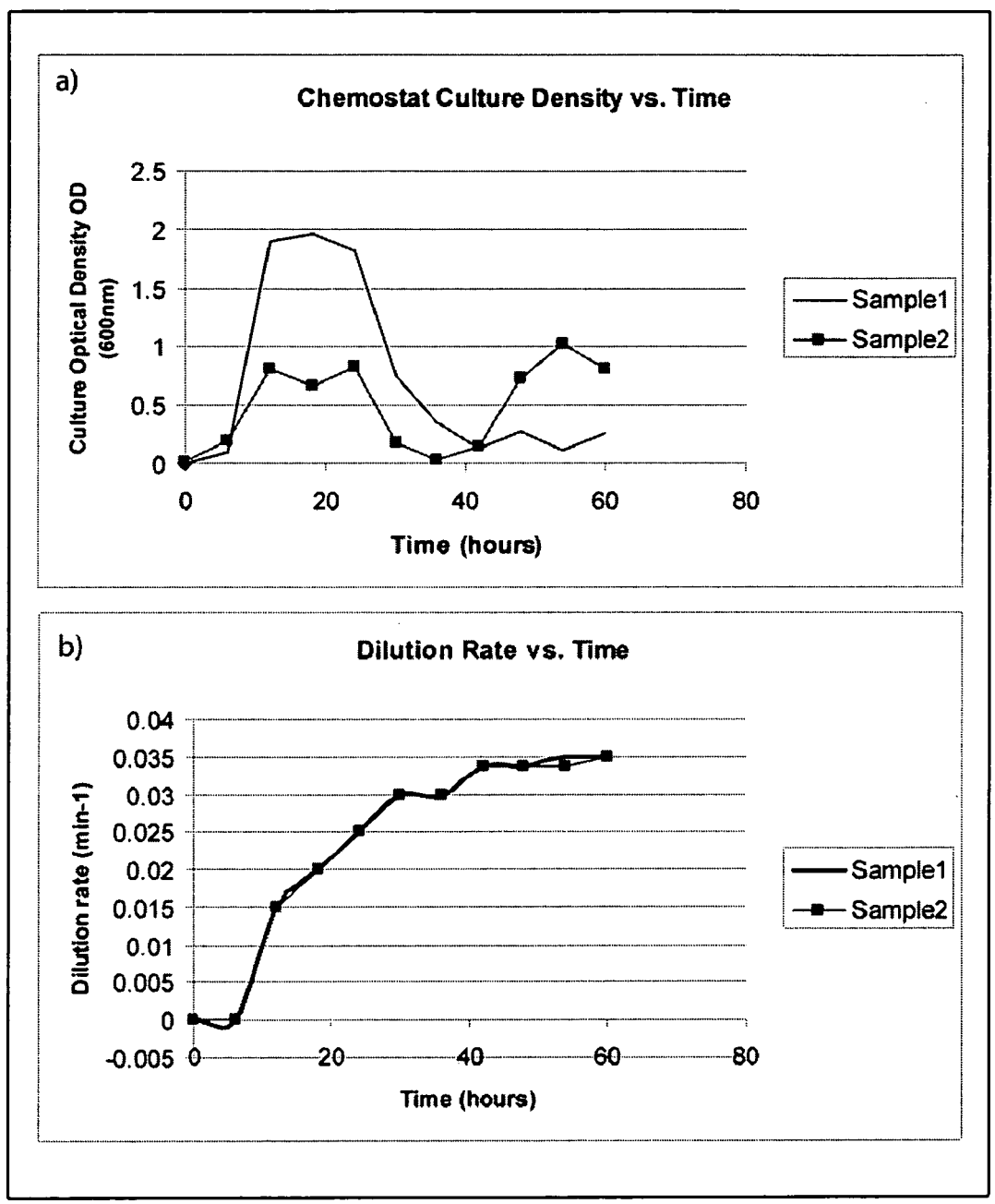
FIG. 2A shows a plot of the culture optical density over time. Culture density was monitored by taking samples from the exit streams of the continuous cultures and taking absorbance readings at 600 nm.
FIG. 2B shows dilution rate for each sample culture plotted vs. time. Increasing the volumetric flow rate of the feed increased the dilution rate over time. The dilution rate per time is calculated by dividing the volumetric flow rate by the culture volume.
Figure 3:
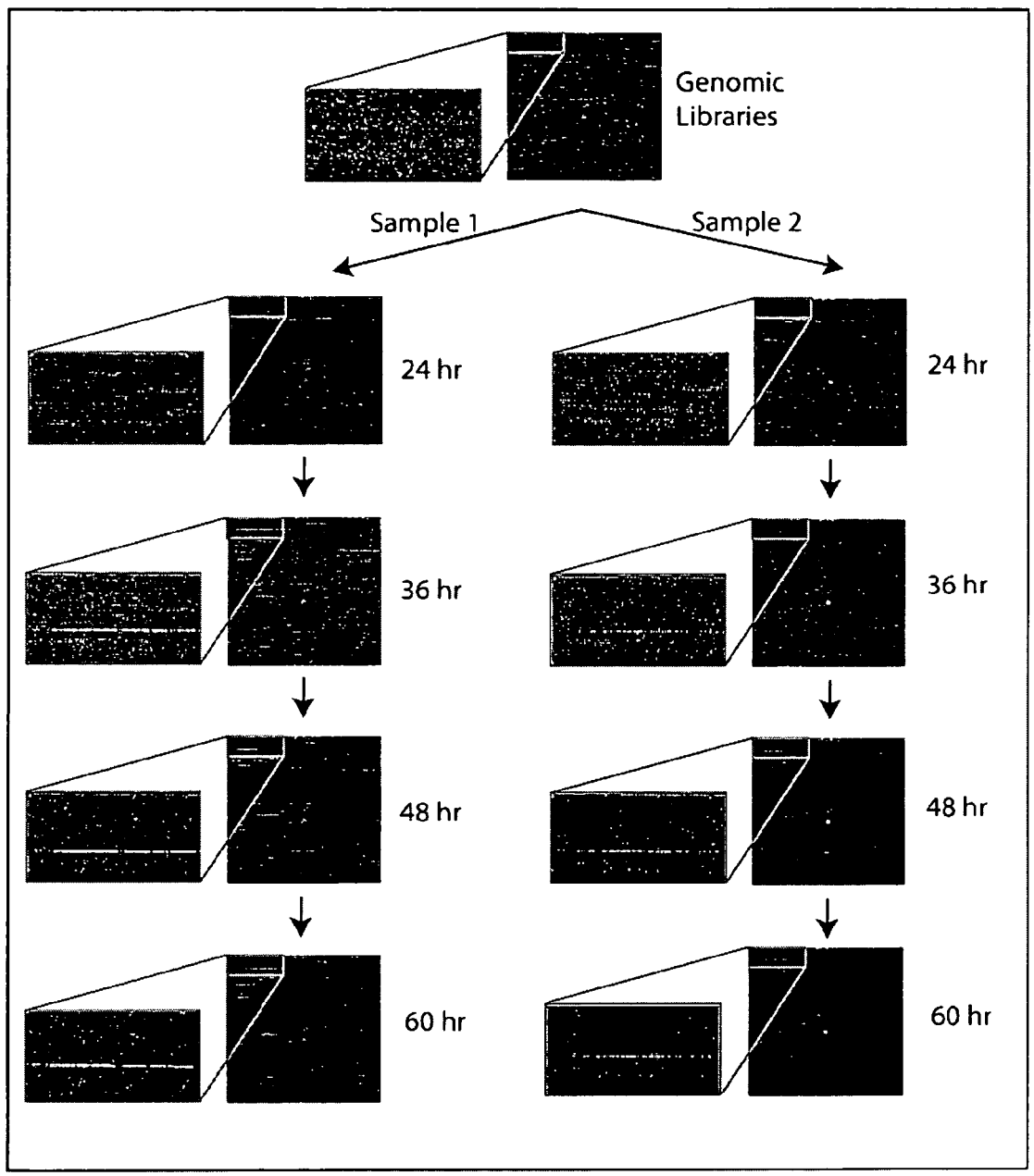
FIG. 3 illustrates micro-array images following the time course of the chemostat selection. Two chemostat cultures were inoculated with a mixture of transformants from each size library. Samples were taken every 12 hours and applied to *E. Coli* Antisense Affymetix Gene Chips. A magnified panel for each chip shows the signal change for the yli operon in greater detail. Each image was scaled to a similar color intensity for clarity.
Figure 4A:
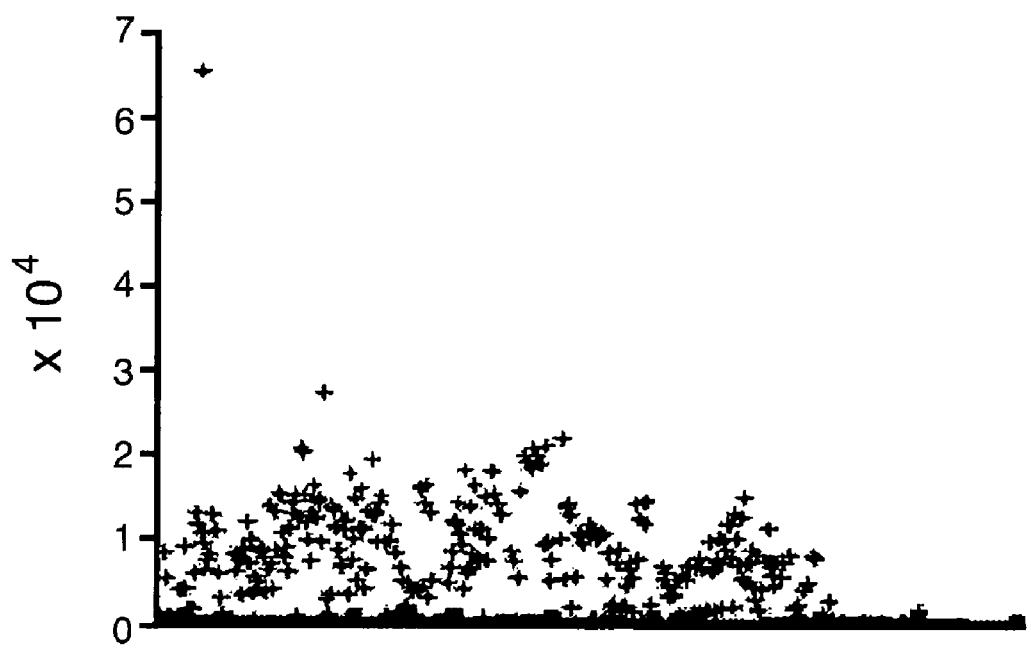
FIG. 4 shows an exemplary Wavelet Denoising and Multi-resolution Analysis of the yli and yea operons. Raw signals (FIG. 4A for yli, FIG. 4B for yea) are averaged and normalized resulting in a continuous signal (FIG. 4C for yli, FIG. 4D for yea). A continuous wavelet transform is performed with a Gaussian mother wavelet, resulting in a multiresolution analysis (FIG. 4E for yli, FIG. 4F for yea). Color corresponds to intensity at any given scale.
Figure 4B:
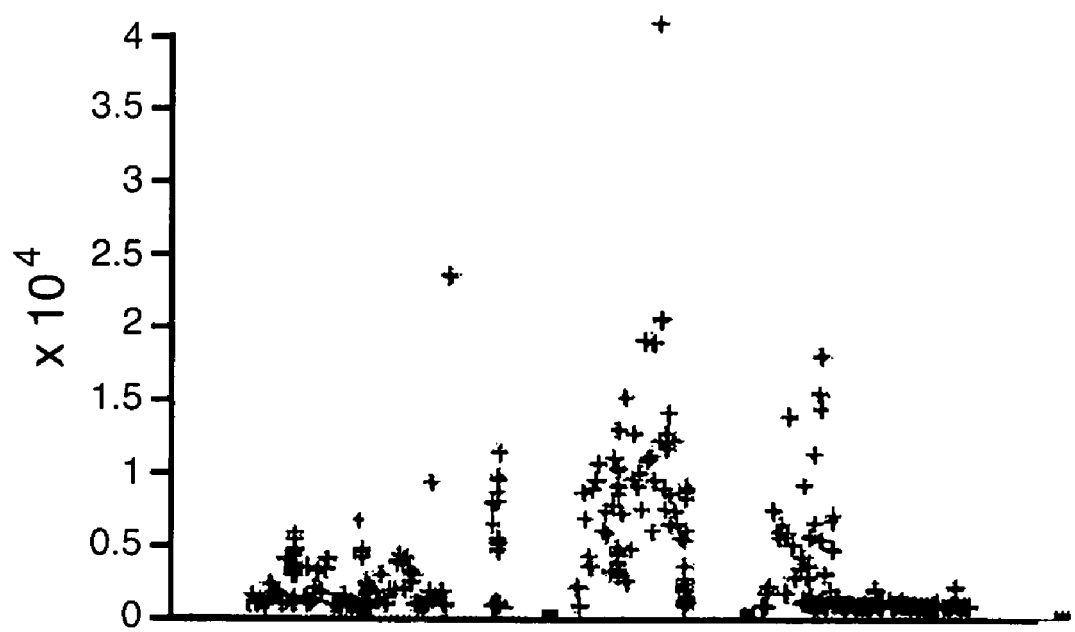
Figure 4C:
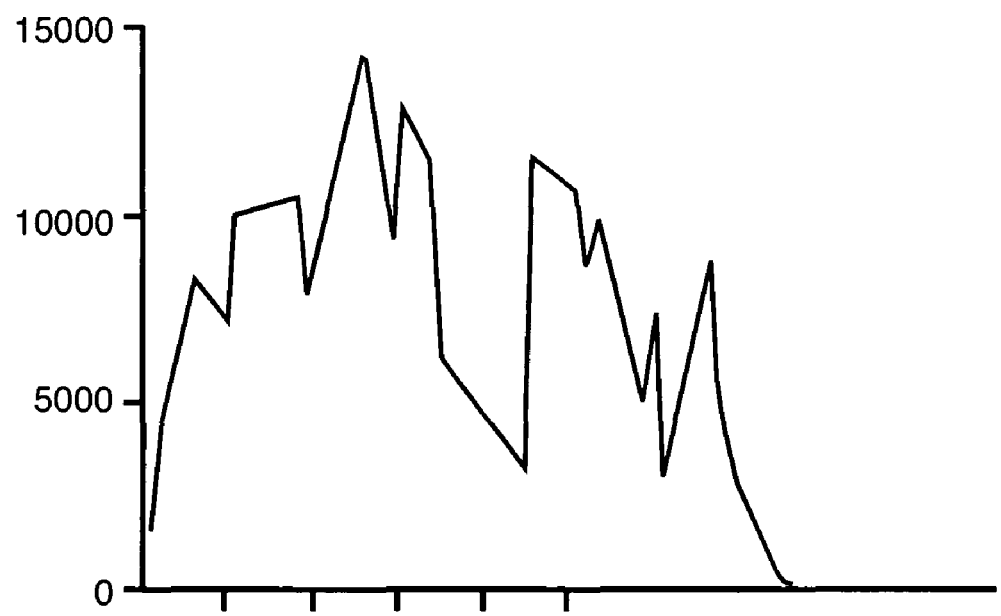
Figure 4D:
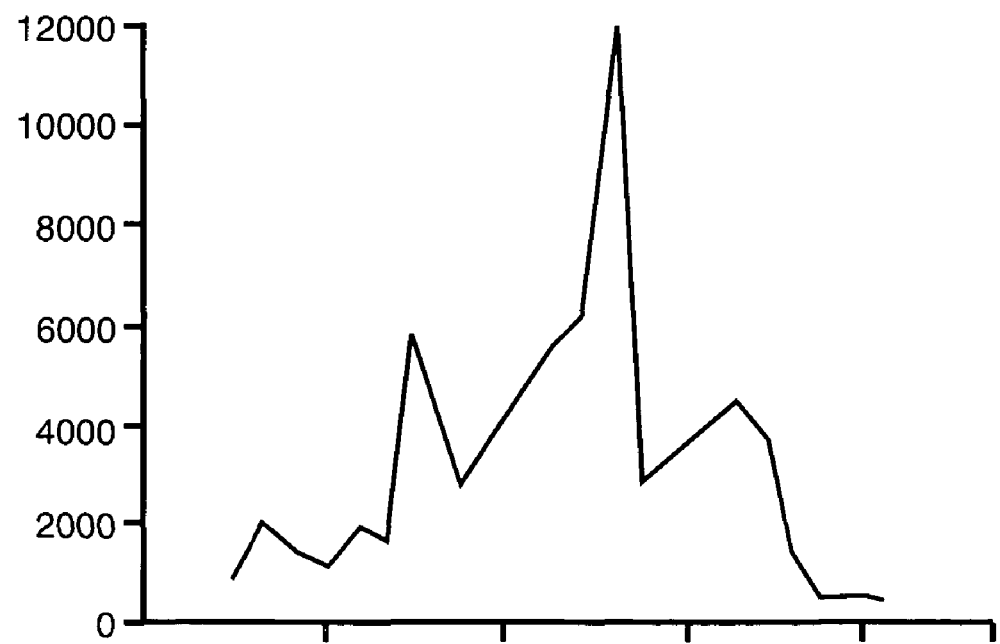
Figure 4E:
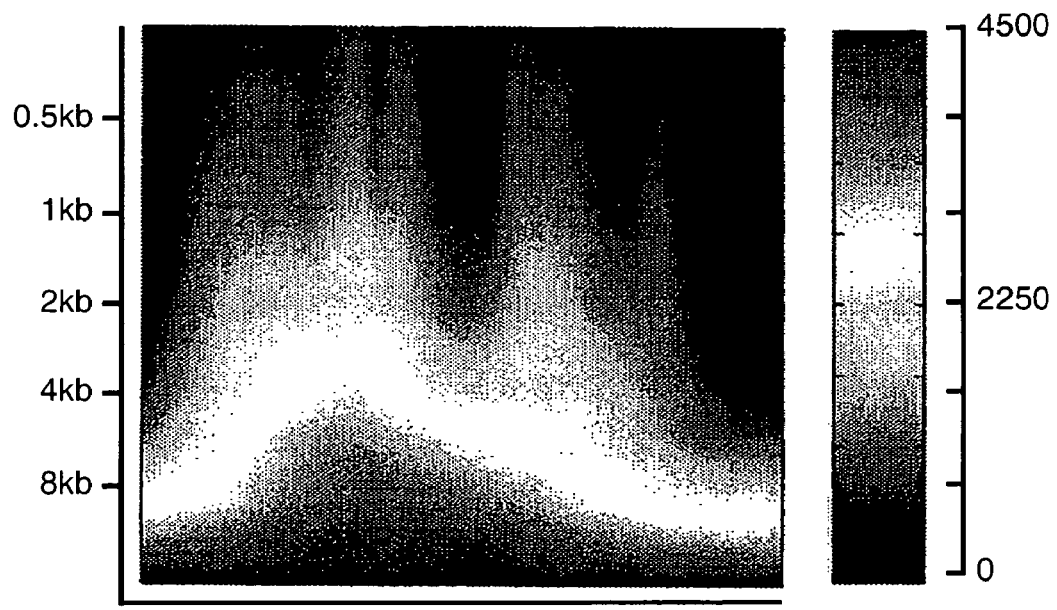
Figure 4F:
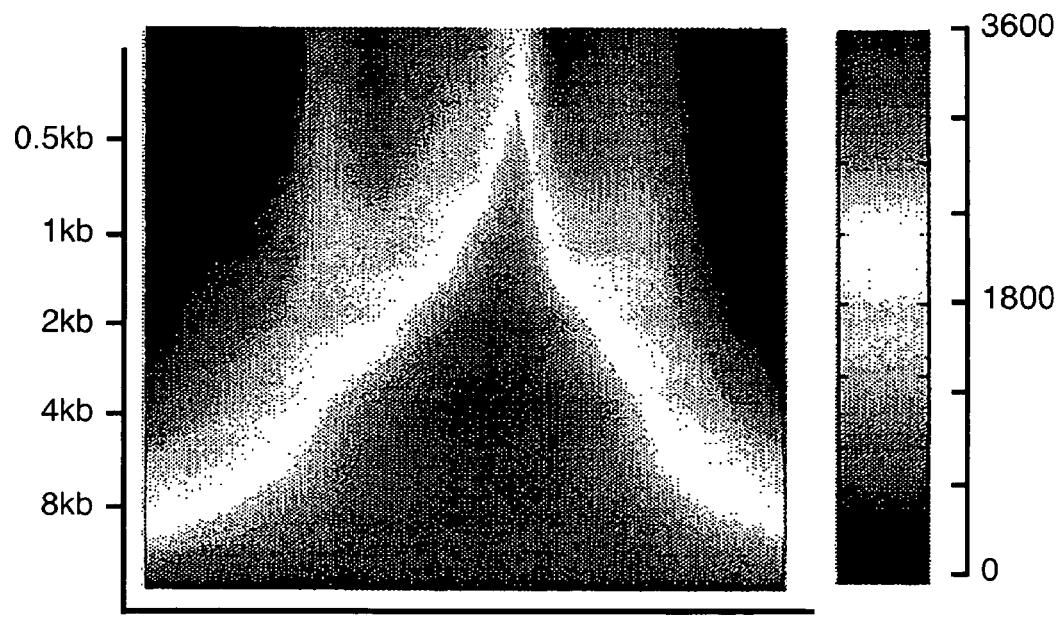
Figure 5:
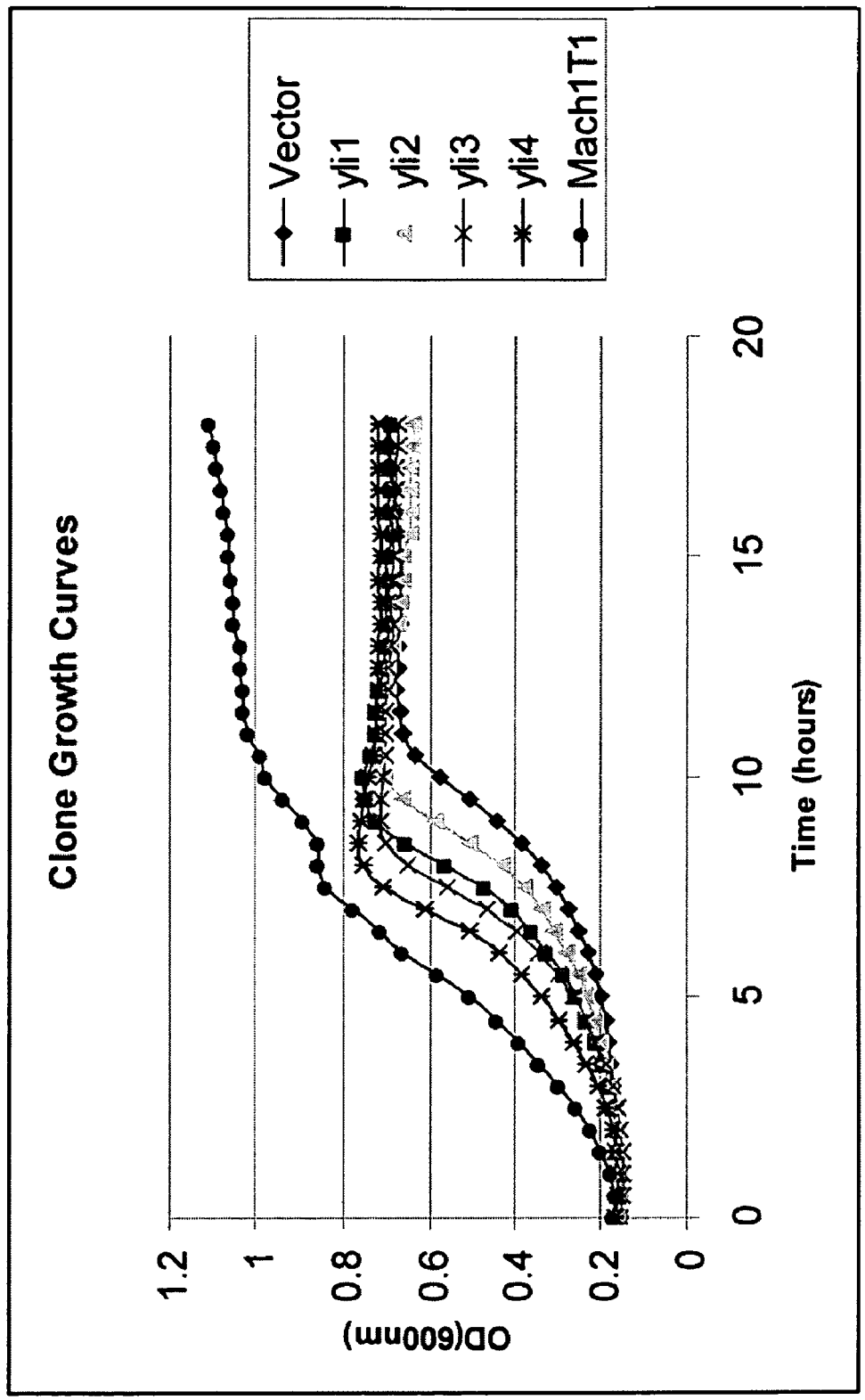
FIG. 5 illustrates growth curves of selected clones. Growth curves were measured in MOPS minimal media in 96 well format for the strain MACH1-T1 as well as the strain with vector alone and 4 clones containing pieces of the yli operon. Note: each curve is the average of greater than 20 experiments.

For each chemostat culture greater than $10^7$ clones were obtained after the transformation of these libraries into MACH1-T1 cells, once again providing adequate representation of the genome at each scale. All transformants were mixed and inoculated into chemostats containing MOPS minimal media. Cell Density was monitored in the culture as the dilution rate was systematically increased. FIG. 2 shows the increasing dilution rate and culture optical density over the time course of two cultures. Every 12 hours a sample was taken from each culture, amplified, prepared and hybridized to *E. Coli* Gene Chips. FIG. 3 shows an image of each chip for the 24 through 60 hour samples for each replicate. In addition a control chip of mixture of purified library DNA is shown as a starting point. A magnified panel emphasizes one of the genomic segments that is amplified, containing the yli operon. Probe level signals for each array were extracted and normalized. A wavelet based denoising scheme and multiresolution analysis (MRA) was performed on various genome segments. FIG. 4 shows the results of the denoising and MRA for two genomic segments the yli operon and the yea operon Clones were isolated from sampling of chemostats, sequenced and growth rates calculated (FIG. 5). These results show an increase in growth predicted from the analysis.

After 60 hours of selection, the majority of the signal mapped to 5 regions of the genome (SEQ ID NO:1 through SEQ ID NO:5, listed below) corresponding to five members of paralogous gene group 117 from *E. Coli* K12. These genes are adrA, yliF, ydeH, yeaP, yddV. They all encode a GGEDF domain, which synthesizes cyclic-di-GMP. This bacterial second messenger is involved in cellular development and may have a role in the cell cycle. In order to confirm the growth phenotypes, growth curves were obtained with replicates using a 96 well plate reader, running KC4 v3.1 (Biotek) using the kinetic mode (incubating at 37° C., and shaking intensity-medium) with readings taken every 30 minutes. A 1% v/v of overnight culture was used to inoculate 200 µl of MOPs minimal media plus kanamycin, in a flat bottom 96 well plate. Optical density measurements were recorded at 977 nm, 900 nm, and 600 nm, and then adjusted according to the manufacturers instructions (adjusted 600=600/((977−900)/0.18)). The adjusted 600 nm reading was used for construction of growth curves. Maximal growth rates were calculated from these curves. Growth rate was calculated as the maximal slope in log scale comprising at least 4 time points (2 hours). Clones carrying these genes not only grow faster, but in addition form cellular groups and films at higher cell densities (data not shown).

Figure 6:
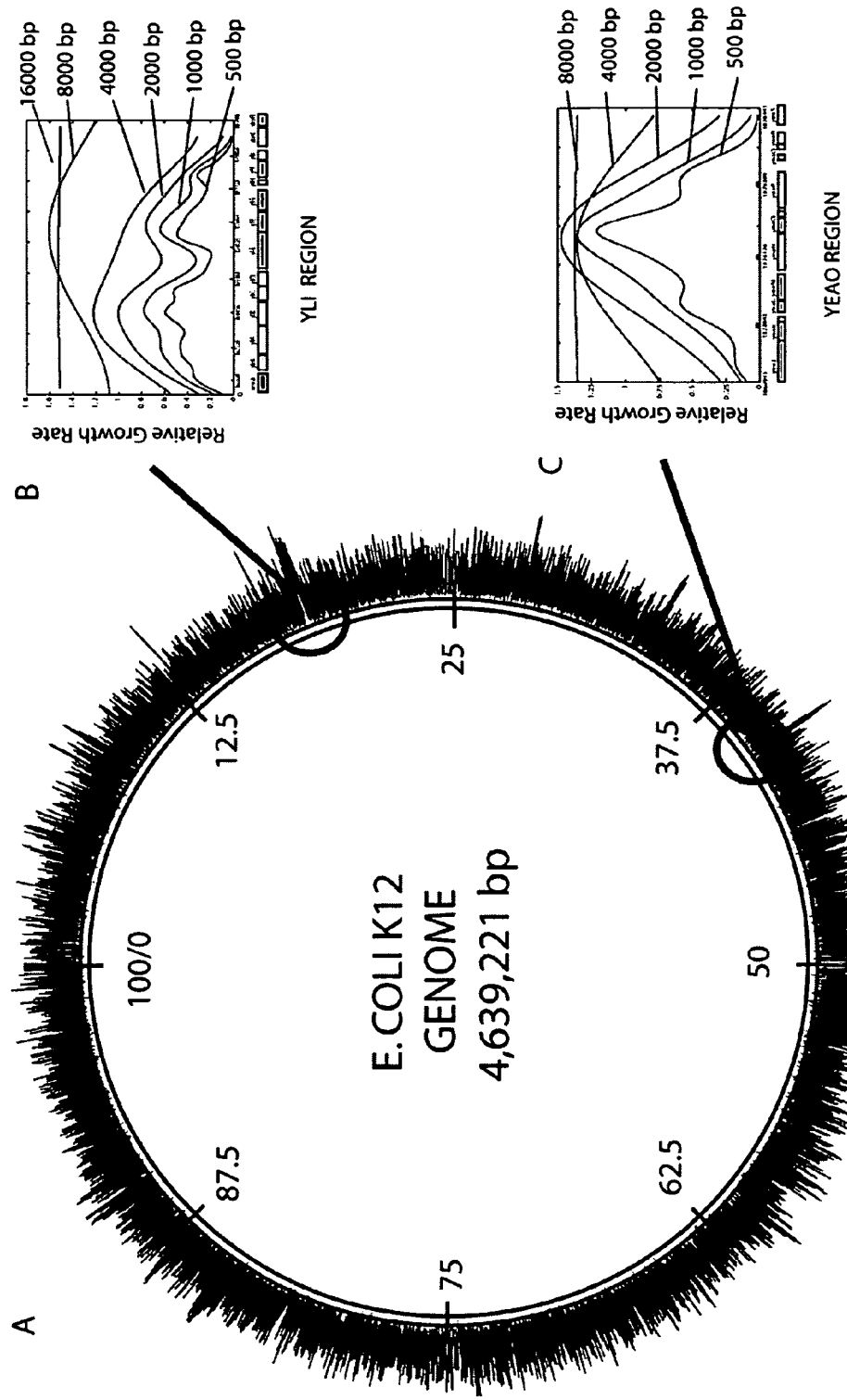
FIG. 6 shows an exemplary genome-wide scan for growth rate conferring elements, as a function of insert size.
Figure 7:
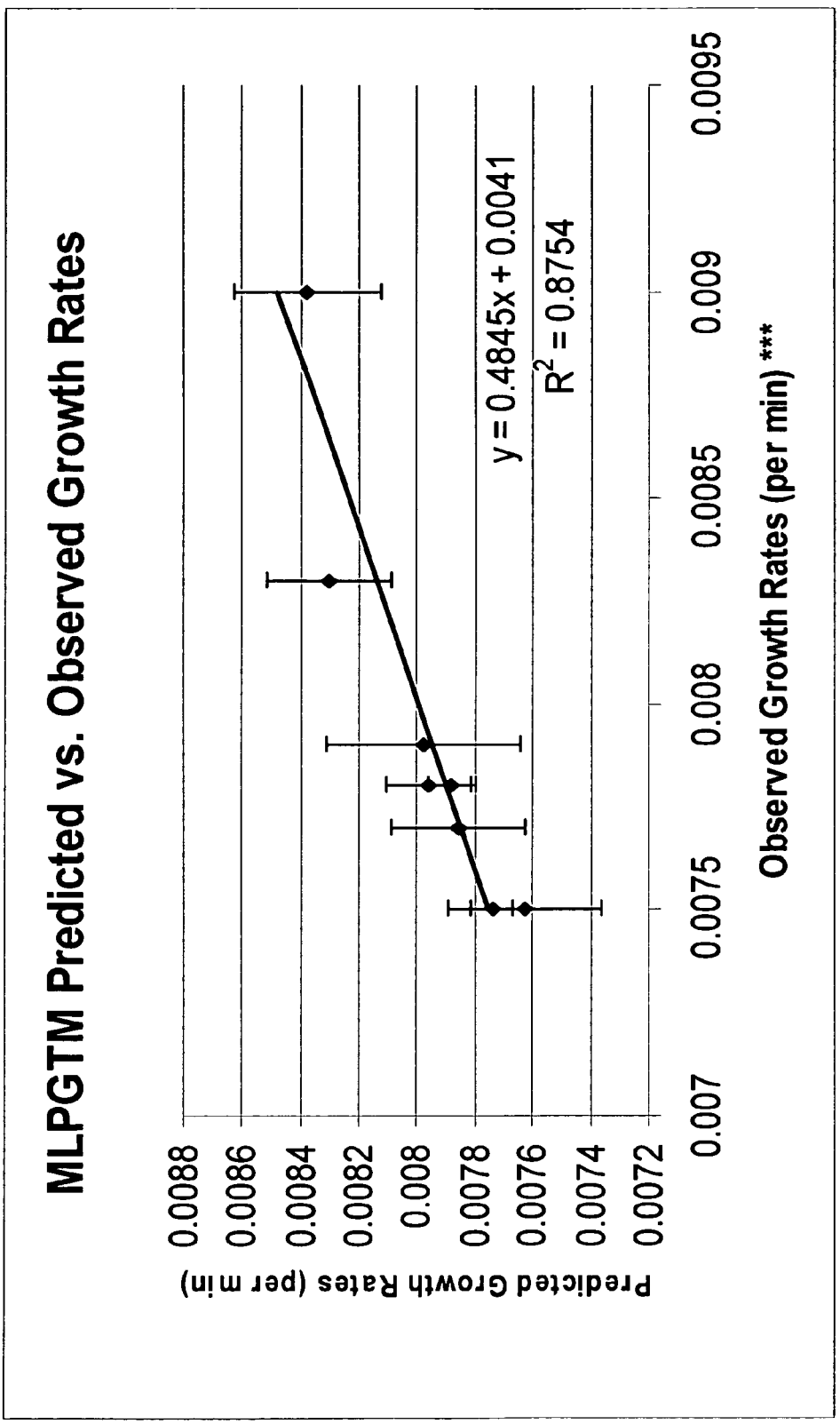
FIG. 7 shows an exemplary plot of MLPGTM predicted versus observed growth rates for genetic elements from *E. coli* K12.

Having measured several growth rates, it is possible to calculate the growth rates associated with all scales and positions along the genome that had nonzero signals. This was performed with the following formula. $\mu=\mu^*-\ln(R^*/R)/(\Delta time)$, where $\mu$ is the growth rate of a scale and position with a ratio of signal intensities over a time period ($\Delta time$) of R. $\mu^*$ and R* are the same known values. This calculation can be performed on a genome wide scale. FIG. 6 shows an exemplary plot of a subset of growth rates around the genome, with the yli and yeao regions amplified. A plot of MLPGTM predicted versus observed growth rates is shown in FIG. 7.

Discussion

ML-PGTM is a powerful and useful method for library selections. The method requires technical precision. Libraries of very defined sizes with minimal chimeras are necessary for clear final mathematical analysis. The libraries must also consist of enough clones to be representative of the genome. A truly representational library requires a bias free stable cloning vector. For this reason we have used vectors which contain transcriptional terminators flanking the multiple cloning site. In this way we ensure adequate representation.

Another factor in the accuracy of the method concerns the probe density of the microarrays. The current *E. Coli* antisense arrays available from Affymetrix were designed for transcriptional profiling experiments. As a result the arrays have a highly variable probe density along the genome. The limitation to this is that is if any plasmids representing regions with no or a low number of probes are enriched, they may be misrepresented in the signal or absent altogether.

We have demonstrated the utility of the MLPGTM method in a mapping of growth rates in minimal media across the entire genome as well as by pinpointing genomic segments that confer a selective advantage. This method can also be readily extended to other selection schemes such as antibiotic resistance and metabolite or substrate tolerance. This selection strategy could be applied to any library to be screened regardless of origin.

Sequences of Growth Enhancing Genetic Elements from *E. coli* K12

```
SEQ ID NO:1 (E. coli K12, 865,108 to 876,944, YliF)

ctc tgcggtagtc aggcgagttc ccgccgggaa
aacaaccgca cctgcagaga tatcttcacc gcgacggcga atattttgcc cgctacgcac
ttcagcagta aaacgcacgc cattgtccat ttgttcagtc tgctcctgca tcaccaccgc
ttcgcagcct tccggcaccg gcgcaccggt cataatacga atgcaggtac ccgcaggcca
ttcaccatgg tatggctgac cggcaaagga tttaccggca acgggcagcg gttgcccgga
ggcaatatcg gctaaacgca ccgcgtagcc gtccattgcg gagttatcaa accccggaac
atcaagcggc gaaacgacat cgctcgccaa aatacgacca aaacactgta ccagtggcag
cgtttcctgg gcggtcagtg gggtgacgcg agaaagcatc tcattaagcg cggtgtcgag
cgacatcaat ccggtggtaa attccatgaa aacactcctg cggaggcaaa atcgaatttg
```

-continued

```
cctattatgt cagaaaaacg ccacagactg tatgccacct cgggcgtagc gctgggtcct
gcctttacat gccatatcca tctttctata ttcaaaaatt gaatgagtaa ttcataaaaa
ttctgatatt tatagcaaaa gtggcgaacc acccttaatg gacgaatact atgggcaaag
cagtcattgc aattcatggt ggcgcaggtg caattagccg cgcgcagatg agtctgcaac
aggaattacg ctacatcgag gcgttgtctg ccattgttga aaccgggcag aaaatgctgg
aagcgggcga aagtgcgctg gatgtggtga cggaagcggt gcgtctgctg gaagagtgtc
cactgtttaa cgccggaatt ggcgctgtct ttacgcgtga tgaaacccat gaactggacg
cctgtgtgat ggatggtaac accctgaaag ccggtgcggt ggcgggcgtt agtcatctgc
gtaatccggt tcttgccgcc cggctggtga tggagcaaag cccgcatgtg atgatgattg
gcgaagggc agaaaatttt gcgtttgctc gtggcatgga gcgcgtctcg ccggagattt
tctccacgtc tttgcgttat gaacaactac tggcagcgcg caaggaaggg gcaaccgtcc
tcgaccatag cggtgcgcca ctggatgaaa aacagaaaat gggcaccgtg ggggccgtgg
cgttggattt agacggcaat ttggcggcag ccacgtccac aggcggaatg accaataaat
acccggacg agttggcgat agtcccttag tgggtgccgg atgctacgcc aataacgcca
gtgtggcggt ttcttgtacc ggcacgggcg aagtcttcat ccgcgcgctg gcggcatatg
acatcgccgc gttaatggat tacgcgggat taagtctcgc ggaagcctgc gagcgggtag
taatggaaaa actccctgcg cttggcgtta gcggtggctt aatcgctatc gaccatgaag
ggaatgtcgc gctaccgttt aacaccgaag aatgtatcg cgcctggggc tacgcaggcg
atacgccaac caccggtatc taccgtgaaa aaggggacac cgttgccaca cagtgatgaa
cttgatgccg gtaatgtgct ggcggttgaa aatctgaata ttgcctttat gcaggaccag
cagaaaatag ctgcggtccg caatctctct tttagtctgc aacgcggtga gacgctggca
attgttggcg aatccggctc cggtaagtca gtgactgcgt tggcattgat gcgcctgttg
gaacaggcgg gcggtttagt acagtgcgat aaaatgctgt tgcagcggcg cagtcgcgaa
gtgattgaac ttagcgagca gaacgctgca caaatgcgcc atgttcgcgg tgcggatatg
gcgatgatat tcaggagcc gatgacatcg ctgaacccgg tatttactgt gggtgaacag
attgccgaat caattcgtct gcatcagaac gccagtcgtg aagaagcgat ggtcgaggcg
aagcggatgc tggatcaggt acgcattcct gaggcacaaa ccattcttc acgttatccg
catcaactct ctggcgggat gcgccagcga gtgatgattg cgatggcgct gtcatgccgc
ccggcggtgc tgattgccga tgagccaacc accgcgctgg atgtcactat tcaggcgcag
atcctgcaat taatcaaagt attgcaaaaa gagatgtcga tgggcgttat ctttatcact
cacgatatgg gcgtggtggc agagattgcc gatcgggtac tggtgatgta tcaggcgag
gcggtggaaa cgggtaccgt cgaacagatt tttcatgcac cgcaacatcc ttacacccgt
gcgctgttga ctgctgttcc gcaacttggt gcgatgaaag ggttagatta tccccgacgt
ttcccgttga tatcgcttga acatccagcg aaacaggccc ccccatcga gcagaaaacg
gtggtggatg gcgaacctgt tttacgagtg cgtaatcttg tcacccgttt cccttttgcgc
agcggtttgt tgaatcgcgt aacgcggaa gtgcatgccg ttgagaaagt cagttttgat
ctctggcctg gcgaaacgct atcgctggtg ggcgagtctg gcagcggtaa atccactacc
gggcgggcgt tgctgcgcct ggtcgaatcg cagggcggcg aaattatctt taacggtcag
cgaatcgata ccttgtcacc cggcaaactt caggcattac gccgggatat tcagttttatt
tttcaggacc cttacgcttc gctgaccca cgtcagacca tcggtgattc gattatcgaa
ccgctgcgtg tacacggttt attgccaggt aaagacgcgg ctgcacgcgt tgcgtggttg
ctggagcgcg tgggcctgtt acctgaacat gcctggcgtt accgcatga gttttccggc
ggtcagcgcc agcgcatctg cattgctcgc gcgttgcat tgaatccaaa agtgatcatt
gccgacgaag ccgtttcggc gctggatgtt tctattcgcg ggcagattat caacttgttg
ctcgatctcc agcgtgattt cggcattgcg tatctgttta tctcccacga tatggcggtg
gtagagcgga ttagtcatcg tgtggcgtg atgtatctcg ggcaaattgt tgaaattggt
ccacggcgcg cggtcttcga aaacccgcag catccttata cgcgtaaatt actggcggca
gttccggtcg ctgaaccgtc ccgacaacga ccgcagcgtg tactgctgtc ggacgatctt
cccagcaata ttcatctgcg tggcgaagag gtggcagccg tctcgttgca atgcgtcggg
ccggggcatt acgtcgcaca accacaatca gaatacgcat tcatgcgtag ataacattca
ggcggagaat aaaatggcaa gagctgtaca ccgtagtggg ttagtggcgg tgggcattgc
gacagcgttg atggcatctt gtgcattcgc tgccaaagat gtggtggtgg cggtaggatc
gaatttcacc acgctcgatc cgtatgacgc aaatgacacg ttatctcagg ccgtagcgaa
atcgttttac caggggctgt tcggtctgga taaagagatg aaactgaaaa acgtgctggc
ggagagttat accgtttccg atgacggcat tacttacacc gtgaaattgc gggaaggcat
taaattccag gatggcaccg atttcaacgc cgcggcggtg aaagcgaatc tggaccgggc
cagcgatccg gcgaatcatc ttaaacgcta aacctgtat aagaatattg ctaaaacgga
agcgatcgat ccgacaacgg taaagattac cctcaaacag ccgttctcag cgtttattaa
tattcttgcc catccggcga ccgcgatgat ttcaccggca gcgctggaaa aatatggcaa
ggagattggt ttttatccgg tgggaaccgg accgtatgaa ctggatacct ggaatcagac
cgattttgtg aaggtgaaaa aattcgcggg ttactggcag ccaggattgc ccaaactgga
cagcataacc tggcgtccgg tggcggataa caacacccgc gcggcaatgc tgcaaaccgg
tgaagcgcag tttgctttcc ccattcctta cgagcaggcc acactgctgg agaaaaacaa
aaatatcgag ttgatggcca gtccgtcaat tatgcagcgt tatatcagta tgaacgtgac
gcaaaagccg ttcgataacc cgaaggtccg tgaggcgctg aattacgcca ttaaccgtcc
ggcgctggtg aaagttgcct tgcgggcta tgcaacgcca gctactgtg tggtaccgcc
aagtatcgcc tacgcgcaaa gttataaacc gtggccttac gatccagtga aagcgcgcga
attactgaaa gaggcgggat atcccaacgg tttcagtacc acgctgtgt cgtcacataa
ccacagcacc gcgcagaaag tgctgcaatt tacccagcag cagttagcgc aggtcgggat
taaagcccga gtgactgcga tggatgccgg acagcgggcg gcagaagttg aaggtaaagg
gcaaaaagag agcggcgtgc ggatgttcta cactggctgg tcggcttcaa ccggcgaagc
ggactgggca ctatcgccgc tgtttgcctc gcagaactgg ccaccgacgc tgtttaatac
cgcgttttac agcaataaac aggtggatga cttcctggct caggcactga aaactaatga
tccggcggaa aagacccgct tatataaggc ggcgcaggat atcatctggc aagaatcgcc
gtggatcccg ctggtggtag aaaaactggt gtcggcacac agtaaaaacc tgaccggttt
ttggatcatg ccagacaccg gcttcagctt tgaagacgcg gatttgcaat aagcaacgca
gggagtggaa tgcttaatta cgttatcaaa cgcttactgg ggttgattcc gacgctgttt
atcgtctcgg tgctggtgtt tttatttgtc catatgctgc ccggcgatcc ggcgcgattg
attgccgggc ccgaagctga tgcgcaggtt atagaactgg tgcgtcagca gctgggttg
gatcagccgc tgtatcacca gttctggcac tatatcagca atgctgtgca gggggatttt
ggcctgtcga tggtgtcgcg tcgtccggtt gccgatgaga ttgccagccg ctttatgcca
```

-continued

```
acgctgtggc tgaccataac cagtatggtc tgggcggtta tatttggtat ggcggcggga
attatcgccg ccgtctggcg taaccgttgg ccggatcgat tgagtatgac cattgcggtg
tcggggatct cgtttccggc atttgctctg gggatgcttt taattcaggt attctccgtt
gaactgggct ggctgcctac cgtgggagca gacagttggc ageactacat tttaccctcc
ctgacgctcg gcgcggcagt ggccgccgtg atggcgcgct ttacccgccg gtcgtttgtc
gatgttttaa gcgaagatta tatgcgtacc gcgagggcga aagggggtgag cgaaacctgg
gttgtcctca aacacgggct acgtaacgcg atgatcccgg tagtgaccat gatgggctta
cagtttggct ttttgctcgg tggttccatc gttgtggaga aagttttcaa ctggccggga
cttggacgct tactcgttga ctccgtagaa atgcgtgatt acccggtgat tcaggcggaa
attctgcttt tctcgctgga atttattctt atcaacttag tggtggatgt gctttacgcc
gccattaacc cggctatcag gtacaagtaa ggatgcgact atttaactgg cgacgtcagg
cggtgttaaa cgccatgcca ctggtcaaac ctgaccaggt acgtacaccg tggcatgaat
tctggcgacg atttcgccgt cagcatatgg cgatgaccgc cgcattattc gttattttat
tgattgtggt ggccattttt gcacgctgga tcgctcccta tgacgccgaa aattattttg
attatgacaa tctgaataac ggaccttctt tgcagcactg gtttggcgtc gattcactgg
ggcgtgacat tttcagccgt gtcctggttg gtgcgcaaat ctcgctggcg gcgggcgtgt
ttgccgtgtt tatcggtgcg gcgatcggga cgttgctggg cttgctcgct ggatattatg
aaggctggtg ggatcggctg atcatgcgca tttgcgatgt gctgtttgcc ttcccgggta
ttttactggc gatcgctgtt gttgcggtgt tgggaagcgg cattgctaac gtgattattg
cagtcgccat ttttttccatC cccgcgtttg cccgcctggt gcgcggcaac acgctggtgt
tgaaacagca aaccttttat tgagtcagcac gcagtattgg tgccagcgat atgaccgttt
tgttgcgtca tatcctgcct gggaccgtct cttctatcgt ggtgttttc accatgcgca
ttggtacctc gattatctCt gccgccagcc tctcatttct cggcctcggt gcgcagccgc
cgacaccaga gtgggagca atgctcaatg aggctcgagc ggatatggtt atcgcgccgc
atgtcgctgt ttttccggcc ctggctattt ttctgaccgt actggcgttc aatttgttgg
gcgatggttt acgcgatgcg ctggatccga aaattaaagg atagttacgt ttgaatattg
cttgaaaggg taatcacctc acaggaaatt attgccctaa gcaagtgttg taactttctg
ctgattttgt agaatcgggt aatttggtta aaaagccgca gcaagggaca attttttgcag
cggcacagcg ttcagatagt tattttgtta aatgtattaa catgctgagt ttatacgaaa
agataaagat aaggctgata attttatttt tattggcagc atcgtcattt attggtcttt
ttttcatcat taactatcaa ctggtatcgg agcgcgcggt aaaacgtgcc gatgccgct
ttgaacttat tcagaaaaac gttggctatt tctttaaaga tattgaacgt tcggccctga
cattaaagga ctcactgtat ttattaaaaa atacagagga gattcaacgc gccgtgattc
ttaaaatgga aatgatgcca tttttagact cggtgggact ggtacttgat gataataaat
attatctttt ttcgcggagg gcgaatgata aatcgttgt ttatcatcag gaacaagtaa
atggaccgct tgtcgacgag tcagggcggg ttatttttgc cgattttaac ccatcgaaac
gaccgtggtc ggtggcttca gatgactcta acaacagctg gaatccggca tacaattgct
ttgatcgtcc gggtaaaaaa tgtatctctt ttacgctaca catcaacggc aaagatcacg
attttgttagc ggtggataaa attcatgtcg attttaaactg gcgatatctg aacgagtatc
ttgatcaaat cagcgctaat gatgaagttc tattttttgaa acaaggccat gagatcattg
ccaagaatca actcgctcgt gaaaaactga ttatttataa tagcgaaggt aattataata
ttattgattc tgtcgatact gaatatatcg aaaaaacatc agccggtgcca aacaacgcat
tattcgaaat ctattttttat tatcctggcg gtaaatttat gaacgcatca gataaacttt
tttatctgcc gtttgcgttc attattatcg tattgctggt ggtttattta atgaccactc
gtgtgttccg tcgcaatttt tctgaaatga cagagctggt taatacgctg gcgttttttgc
ctgactcaac ggatcaaatc gaggctctga aaattcgtga aggcgatgcg aaagagatta
tcagcatcaa aaattcgatc gcggaaatga aagatgccga aattgaacgg tcaaataaat
tgctctcact gatctcttac gatcaggaaa gtggttttat taaaaatatg gcgattattg
agtctaacaa taatcagtat ctggctgtgg ggatcatcaa actgtgtggt ctggaagccg
tggaagcggt gtttggtgtt gatgagcgca ataaaatcgt caggaaattg tgtcagcgaa
ttgccgagaa atatgcgcaa tgctgcgata tcgtgacatt caatgccgat ctctatttac
ttctgtgtcg ggaaaatgta cagacattta cccgtaaaat agcgatggta aacgattttg
acagcagctt tggctaccgc aatctgcgca tccataagtc tgccatttgt gaacctttgc
agggggaaaa cgcctggagt tacgcagaaa aactgaaact ggcgatttcc agtatccgtg
accatatgtt ctcagagttt attttctgtg atgacgcgaa actcaacgaa atagaagaga
atatctggat tgcgcgtaat attcgccatg caatgaaat tggcgaacta ttcctcgtct
atcaaccgat cgttgatatt aacacccgcg ccattctggg cgcggaggcg ttgtgccgtt
gggtgtctgc ggagcggggg atcatttcac cgctgaagtt cattaccatt gctgaagata
tcgggtttat caatgagctg ggttatcaga ttattaaaac ggcaatgggt gaattcagac
attttagtca gcgtcgctcg ctgaaggatg atttcttact gcatattaat gtttcgccct
ggcagttaaa cgaaccacac tttcatgagc gttttaccac catcatgaaa gaaaatggcc
tgaaggcgaa cagcctctgt gttgagatca ctgaaaccgt gatcgagcga attaatgaac
atttttatct caatattgaa caactgcgta acaagggggc acggatatcg attgatgact
ttggcaccgg tttgtcaaac ctgaaacgtt tttatgaaat taatccagac agcataaagg
tggactcgca attcaccggc gatattttcg gtactgcggg aaaaattgtg cgcattattt
tcgacctggc acgctataac cggatcccgg tgattgcgga aggcgtagag agcgaagacg
ttgcgcgcga attaatcaaa ttaggatgtg ttcaggctca ggggtatctg taccagaaac
ccatgccatt ctccgcctgg gataaaagtg gaaaattagt aaaagagtag tttacgtatg
tccagaatca ataagttcgt acttacagtc agtctgctga tttttatcat gatttcagca
gttgcctgcg ggatctacac tcaaatggta aaggaacggg tgtatagcct gaaacagtcc
gttattgata ctgcttttgc ggtggcaaat attgctgaat atcggcgtag cgtggcaatt
gatcttatca acacgctaaa tcccacggag aacagctgt tggttgttt gcgcacagct
tacgccgact cggtttcccc ctcttatttg tacgatgtcg gtccttatct gatttccagt
gacgaatgta ttcaggtaaa ggagttcgag aaaaattatt gtgcagatat tatgcaggtt
gtgaagtatc gacatgtcaa aaatacaggg tttatctctt ttgacggtaa aaccttcgtc
tattacctct atccggtaac tcacaatcgt agtctgatat tttgcttgg tctggagcgt
ttttctttac tgtcaaaatc gctggcgatg gacagcgaga acctgatgt ctctctattt
aagaacggta aaccggtgac cggtgatgaa tataatgcta aaaacgccat cttcaccgtt
tcggaagcga tggagcactt cgcctatttg ccgaccggat tgtatgtatt tgcgtataaa
aaagatgttt atttgcgggt ttgtacattg attattttct ttgccgcatt ggtggcagtg
atatcgggtg ccagttgcct ctatctggta cgcagagtga ttaatcgtgg tattgtggag
```

-continued

```
aaagaagcca tcattaataa ccattttgaa cgcgtactgg atggcgggct tttcttttcg
gctgccgatg tcaaaaaact ctacagtatg tataactcgg cgttcctgga cgacctgacc
aaagcaatgg gcagaaaatc ctttgacgaa gatttaaaag cgctgccgga aaaaggcggt
tatttgtgcc tgtttgacgt cgataaattc aaaaacatta acgacacctt cggtcatttg
ctgggcgatg aagtgttgat gaaagtggtg aaaatcctta aatcacagat cccggtagat
aaaggtaaag tctaccgctt cggcggtgac gaatttgcgg tgatttatac gggtggaacg
ctggaagagt tgctatcgat tctaaaagaa atcgttcatt tccaggtggg aagcattaat
ttaagtacca gtatcggtgt agcacattca aatgaatgtc ctaccgtcga acgcttgaaa
atgctggcgg atgagcggct gtataagagt aagaaaaacg gcagggcaca gattagctgg
cagtaatcat tattcgcagg ccggacaaat gattttgccc ggcctgaatt aattaaaccc
ggctacccca caaatcgtac tcatcggcgt gctcgacttt cacacgcagg atatcacccg
gcttaacgtt ggtttcacca ttgagataaa ccgcgccgtc gatttccggt gcatctgcca
tgctgcgacc aatcgcgcct tcttcgtcca cttcgtcgat aatcaccaga atttcacggc
ccactttctc ttgcaggcgc tcggcggaaa tctgctgctg cagctgcatg aaacggttcc
agcgttcttc tttaacttct tccggaacct ggtcaggcag gcattggcg tctgcacctt
caaccgggct gtatttaaag cagccaacgc gatccagacg cgcttctttc aggaagtcga
gtagcatctg gaaatcttct tctgtctcgc cagggaagcc gacaataaag gttgagcgta
gggtcagttc cgggcagatt tcgcgccact gtttgatgcg cgccagttgg cgatctacag
aacccggacg cttcatcagt ttgagaatgc gcgggctggc gtgctgcaac ggaatgtcca
gatacggcag gattttgcct tctgccatca gtgggatgac gtcgtccaca tgcggataag
ggtaaacgta gtgcagacgt gtccagatcc ccagtttcga taactgttcg cacaggctga
ccatgctggt ttttaccggc tcgccgttgt ggaagccagt acgatgttta acatcaacgc
cataggcgga agtatcctgc gagatcacca gaatctcttt aacgcccgca tctaccagac
gtttcgcttc acttaacact tcgccaatcg gacggctcac caggtcgccg cgcatagacg
gaataatgca aaggtgcag cggtgattac agccttcaga aattttcaga taggcataat
gacgcggcgt cagtttcaca ccttgttctg gcaccaggct caggaatggg ttgtgtttcg
gttttggcac gtagtgatga acgtgctcca gaacctgctc atag
SEQ ID NO:2 (E. coli K12, 402,893 to 405,965, adrA)

ctccgtct
ctataatttg ggaaaattgt ttctgaatgt tcccaaaaat aatgaatgat gaaaacttt
tcaaaaaagc ggcggcgcac ggggaggaac ctcctttaac tcctcaaaac gaacatcagc
ggtccgggct gcgcttcgcc cgtcgcgtca gactaccccg tgcggttggc ctggctggca
tgttcttacc gattgcttca acgctggttt cacacccgcc gccgggctgg tggtggctgg
tgttggtcgg ctgggcgttc gtctggccgc atttagcctg gcagatagcg agcagggcg
tcgatccgct tagccgggaa atttacaact taaaaaccga tgcagtatta gcggaatgt
gggtaggcgt aatgggcgta aacgctctgc cttccaccgc gatgttgatg attatgtgtc
tgaatttgat ggggcaggc ggccccgtc tgtttgtcgc gggtctggtg ttgatggtgg
tttcctgcct tgtcaccctc gagctgacgg gcattaccgt gtcgttcaat agtgcgccgc
tggaatggtg gctctccctt cccattattg tcatttatcc tctgctgttt ggctgggtca
gctaccagac ggcaaccaaa ctggcggaac ataaacgcag gttgcaggtc atgagtaccc
gcgacggcat gacgggcgtg tataaccgac gtcattggga aactatgtta cgcaatgaat
ttgataactg tcggcggcat aatcgcgatg caacgttact gattatcgat atcgaccatt
tcaagagcat caacgatacc tggggccatg atgtgggcga tgaagcgatt gtggcgctta
cccgacagtt acaaattacc ctgcgcggta gcgatgtgat tggtcggttt ggcggcgatg
agtttgcagt aatcatgtcc ggtacgccag ctgagagcgc cattaccgcc atgttacggg
tgcatgaagg gctaaataca ttacgtttgc cgaatacgcc acaggtaact ttacggatta
gtgtgggggt tgcgccgctg aacccacaaa tgagtcacta tcgtgagtgg ttgaaatcgg
cagatttggc gctttacaaa gcaaagaaag ccggacgtaa ccgcaccgaa gtggcggcct
gacgtccggc gaaagtcatc aggatttgct gagttttttct gattttttcca tacacttcgt
catcgcttcg atcactgcag cacggaagcc ttttctcttcc agtacgcgta ccgcttcaat
ggtggtgcct cccggtgagc agaccatatc tttcagtgcc cccggatgtt ctcccgtttc
cagcaccatt tttgcggaac ccattaccgc ctgagcggca aatttatacg cctgggcgcg
tggcatcccg cccagcacgg cggcgtcggc catcgcttcg ataaacataa atacgtaggc
tggcgaagaa ccgctcacac cgaccaccgg gtggatcatc ggctcagcaa ttacttccgc
ttcgccaaag cagcggaaaa tattcagcgg ta tcttctgggg ttaccagcgc
gtttggcgtt acgaggtca tcccggcatt aaccagtgcg ggagtgttcg gcatggcgcg
gataattttc cggtcatggc ccagcgcgcg ggcaagctgg tcgagcgtga cacctgcagc
aatagaaacg accagagagt ctttattcag gctggaggtg atttgctaa gcactttaat
catgatgcca ggtttaacgg cagcaaaaat gatgtcgcg atttgcgcca cttcttgcgc
cgattctgcg gcgttgatgc cgaactggtc atgcagggcg gcgactttat ccggggaggg
ggtgtatacc cagatttgcc ctgaagcac ctgaccgctg gcaatcagac cgccgagaat
ggcttttccc atattgccgc agccaataaa accgattttc tttttccattg cctcactcct
gccgtgaaat tcattgtttt gataatcgct ggcagaagca taaacagaac tatgccggaa
ggcaaaagcg cgacacaata gaggattacc caacaaagga tgactttatg acaatttggg
tggatgccga cgcgtgtccc aatgtaatta aagagatttt gtatcgcgcg gcggaacgta
tgcagatgcc gctggtactg gtagcaaacc agagtttacg cgtgccgcca tcgcgattta
ttcgtacgct gcgcgtcgcg gcaggtttcg acgttgccga taacgaaatt gtccggcagt
gtgaagcggg cgatttggtg atcaccgcag atataccttt ggctgctgaa gccatcgaga
aaggcgctgc ggcgcttaat ccgcgcggcg aacgttacac gccagcgacc attcgtgagc
gcctgacgat gcgcgatttt atggatacct acgtgccaa tgggatccag accggcggac
cagatagcct ttcacaacgt gaccgccagg cctttgccgc ggagctggag aagtggtggc
tggaagtgca acgtagtcgt ggctaaatgt aatttattat ttacacttca ttcttgaata
tttattggta tagtaagggg tgtattgaga ttttcacttt aagtggaatt ttttctttac
aatcgaaatt gtactagttt gatggtatga tcgctattct catgacaccg gctttcgccg
cattgcgacc tattgggaa aacccacgat gacacaacct cttttctga tcggcctcg
gggctgtggt aaaacgg tcggaatggc ccttgccgat tcgcttaacc gtcggtttgt
cgataccgat cagtggttgc aatcacagct caatatgacg gtcgcggaga tcgtcgaaag
ggaagagtgg gcgggatttc gcgccagaga acggcggcg ctggaagcgg taactgcgcc
atccaccgtt atcgctacag gcggcggcat tattctgacg gaatttaatc gtcacttcat
gcaaaataac gggatcgtgg tttatttgtg tgcgccagta tcagtcctgg ttaaccgact
```

-continued gcaag

SEQ ID NO:3 (*E. coli* K12, 1,874,136 to 1,877,094, yeaP)

```
ctgca gcggcactgg gatcggctat
ggtcgtgccg ctggctttga acggttttgg ctggcaaggc gcgttgctca tgctgatgtg
ttttcctctg ctggctcttt ttttatggct gccacagtgg cgaagtcaac aacatgcaaa
tttgagtacc tcgcgcgcct tacatactcg gggtatctgg cgttcaccgc ttgcctggca
ggtcacattg tttcttggga tcaactcact ggtctattac gtgattattg gctggcttcc
ggcgatcctc atcagtcacg gctatagcga agcacaggcg ggttcactgc atggtttgct
gcaactagcc acagcagcac ccggtttgct gatcccactt ttcttacatc atgtgaaaga
tcagcgtggt attgcagcgt tcgttgcctt gatgtgcgca gtgggcgcgg ttgggctctg
ctttatgcca gcgcacgcga tcacctggac tctgcttttc ggttttggtt ccggcgcaac
aatgatactg gggttgacgt tcattggtct gcgggctagt tctgcgcatc aggcggcggc
actctcgggg atggcacaat ccgtcgggta tttgttggca gcctgtgggc cgccgctgat
gggtaaaata cacgatgcta acggtaactg gtctgtacca cttatgggtg ttgccatact
ttcactactg atggcgattt tcggactttg cgccgggaga gacaaagaaa ttcgctaata
tccggtgcta tagtgacgta acaaatcatg cgtgaaaggg agaacaaaca cgatgaatat
tcagtgcaaa cgcgtttatg atccggctga acagagcgat ggttatcgca tactggtcga
ccgcctctgg ccgcgcgta tcaaaaaaac cgatttagcc cttgatgagt gggataaaga
aatcacgccg tcaacggaac tgcgcaaagc ctttcacggc gaagtcgtcg attatgcaac
ctttcgcgag caatatcttg cagaactggc gcaacacgag caagaaggaa agcggctggc
ggacatcgcc aaaaaacagc cgctgaccct gctctactca gcaaaaaaca ccacgcagaa
ccatgcgctg gtgctggccg actggctacg tagcttgtga ttttagtaca gcatccggcg
gttatttttc accagccgga tggtcacgcc gccacaatgc ccattcatca atcgtttcac
cgcccggtaa tttgcaattg ttgctgaccc cttgcgctgt ctgcactgga atgagcgtcc
cgcccttctg ctggcaatag accgacgccg gatttgccat accaatctgc ggcggtttag
gtgcttctgg ctgagaaggg gttgaacaac cagccaggac cagcaagcaa ggcagaacaa
aactgataat tttcatttat tgatctcaca tatttatcca agattagagt atcgcggtat
cgttttgttt tgcagcacta tttttattac attcactcaa aacatattac gtcttgtttc
atctttgttg atgatgtttt atcatgcctg caaagattaa ataatcagca tttacccgcc
gtatcctgga gttgttccgt gtcagatcga attatcgccc gcgtctcgca atcccttgcc
aaagaacagt cactggaaag tctggtccga cagcttctgg agatgctgga aatggtcact
gatatggaat caacctacct gaccaaagtg gatgtcgaag cgcgcctgca gcatattatg
tttgcccgta acagccagaa aatgtacatc ccggagaatt ttaccgtctc gtgggattac
tcgttatgca aacgcgccat tgatgaaaac tgctttttca gcgatgaagt ccccgaccgt
tggggtgact gtattgcggc acgcaatctt ggcatcacca catttctgag cacgccaatt
cacttaccgg atggatcatt ctatggcacg ctttgcgccg ccagcagtga gaagcgccag
tggagtgaac gcgcggaaca ggttttacag ttattcgccg gactgattgc acaatatatt
caaaaagagg cactggttga acagctgcgc gaagccaatg ctgcgctgat tgcgcaatcg
tataccgact cgttaaccgg gctaccgaat cggcgggcga ttttgaaaa tctgacgaca
ctgtttttccc tcgcccggca tcttaaccat aagataatga tcgcgtttat cgatctggat
aacttcaaat taatcaatga tcgttttggt cataatagtg gcgatctgtt tctcattcag
gttggcgagc gccttaatac gctccagcaa aatggcgaag ttattggtcg tctcggcggt
gatgagtttt tagttgtttc actaaacaac gagaatgcgg atatttcgtc gctgcgagaa
cgcattcagc agcaaatacg tggagaatat cacttaggtg atgttgattt gtattatccc
ggtgccagtc ttggcatagt agaagtcgat cctgaaacaa ccgatgcaga cagtgccctg
catgctgccg atattgcgat gtatcaggag aaaaaacaca aacagaaaac acctttttgtc
gcgcatccag cgctacattc ctgaggcgta ttcacatcct tttgattggt gataacatgc
gaatcggtat tattttttccg gttgtaatct tcattacagc ggtcgtattt ttagcatggt
ttttattgg cggctatgct gccccgggag cataaagatg aaaaaaacaa cgattattat
gatgggtgtg gcgattattg tcgtactcgg cactgagctg ggatggtggt aacgtcacct
ctaaaaaata gcaaggctg cctgtgtgca gcctttgtgc aatttaagcg ttaacttttta
atcttcctgt agataaatag cacgacaatc gcaccaataa cggcaaccac gaag
```

SEQ ID NO:4 (*E. coli* K12, 1,562,990 to 1,565,632, yddV)

```
c tggcgaatct
gccgttcttc ggtgatatcc gagaaagtca ttaccaggtt ctgcagatgc gcgagcacgt
cataaaccgg gctgatagag gctttaatcc agatttttc accggtgcgc gtcaacagca
gaaattcgtc ctgatcgcgg gcggttttcc atagcaactg ttgtaaacga atgcggttat
cggcagggaa ttcaggaatg ttcaggagtg tatcgggcg cataccgctg gcttcgctaa
tgcagtaacc aaacatttcg gtaaatgcgc gattgcactg cacaatatgg cgttccggat
cgaggacaat caccggtcgg tcgagatggt caacggcaat aatcaattgt cgggtctgtt
cttttttgcgc catttctacg ctggcatccc gtaccagcgc caggtaataa actttccct
cggcgctcac tttcgatagc gcaaaacggg tCCagatttt actgccgtct ttttttccca
gctgcagctc ccgactcatc ccctcaacac gcgctttacc gccttcacgg ttgtgacgaa
tgtattcagg atgcgcagga cgcaaatccc gcggaatcag catatcaatg ttattgccaa
tgacttcttc acgtttgtat ccccagagct ctctgcgc ggggttgaaa acatcactt
catcattttc gttaattaac accgcaccca tcatattttg ctcaagggcg gggaaaaaa
tgccatcggc ggcattatcc gcatcggtta gcttcatgat tacctctgca tcctggcgca
tctaaagact ggctttccag agttcaacac ggtttctacc tcgtcttttg gcgatataca
gagcttcatc ggctatttga atgaggcgct catagtcagg atgaccatta acatggcgg
caccgatgga aagtgagagg gcaatatctt cgccgttttgc ggctttcagt ttggttttct
ccacccgact gcgaatacgt tctgcgtac gtaacgtttc gttttcagaa gcttcagtca
aaacaatgat aaattcatcg ccccgtagc ggaaaacata atcactactg cggacgttgt
cataaaggc ctgagagact ttacgcagaa tttcatcacc agtgttatgg ccccacgtat
cgttgatctc tttgaattta tcaacgtcaa taatcagcac gtacagcggt gtaccggtcc
ggttggcatg ggcaatttcg cgtttgaaga tagtcggtag gaaacggcgg ttaagtaatt
tcgtcagtac atccataccg acttcgtggc gcgatacttc ttcaaacaat tcacgcagca
aggtaataat ttgcgatacg gtatttctta tctgtaataa aaatttccacc cgcagacttc
tgttattcaa atttctggtg ttacgcatgg tttgattgaa ataccgtcg aaatcctgaa
tcagacggga gatatggcct acttcggcaa taccactaaa ataatgtcga cctttatggt
```

```
taaaccacag gccaaaatca gcctggctta aaggcaaact actgcctaaa tcagaatcca
gcaggatttt atagataata tctatttccc atgaaagtat tgaggctatt tgccgttctt
tttcttcttc ggcgttttcc agtaacgaga agatacgata gttttcatct tcctttgagg
cactactgtc actaaaggta aacgcgcgag tcatcacttc catcgcgata tcaatactgt
taatcgagaa atggtagacc tgaagttttt ctgcggcgga ataatccgaa gagaagatca
ccggatagag gatttttttc agcacccgaa accccatctc gacaatttct accggaattc
ctatgcgggc atgcacttcc gcgacggtat gctggatttg tattagcctt tcgacatcgt
caacctgggc agaaagcacg ttaataatcc agcgttccat cgcactcttc aactgccgct
caacttgttc attactcaag aattcttcgg catgcgggtc gatgcggaca attcgataaa
actcgatact cagataatga gcatgcgcaa cggcaattcc gcggcttta gcacgaattg
gcggatctgc ctgttcgaca agtccggtcc actcatcttt cattcttta aaatacatct
ccataattca cacccttata aggctgggaa atcagacgga atcaaaatga aacgcaacgt
gcgagatcga ctaactgcac catattctcc tgaaatatga agatatactg aaaagaaata
agcgatttag gacagtttca atctacgcta ctgttcttca gaagagtata gcccatcgta
attatttttc ggtgacagcg aatatcgtat ggttttcat attcatacat ttttattagg
gatttatggc tgtttaacta agtgtggtta atttgactta agtaagcatg attattagtg
ggatagttta agagggtaac aagccggtgg gtaaagcacc ggcttgttac aaagtaagaa
tgggagttta actgccccag cgactttgca gatagctgac cgcttgttga gtctgcggtt
tattcagata gtcctcacgg aacaagatgg tgccgctaat ttcgggcaca gc
SEQ ID NO:5 (E. coli K12, 1,620,874 to 1,622,633, ydeH)

ttgcatg gatagatttg tgttttgctt
ttacgctaac aggcattttc ctgcactgat aacgaatcgt tgacacagta gcatcagttt
tctcaatgaa tgttaaacgg agcttaaact cggttaatca cattttgttc gtcaataaac
atgcagcgat ttcttccggt ttgcttaccc tcatacattg cccggtccgc tcttccaatg
accacatcca gaggctcttc aggaaatgcg cgactcactc ctgctgtcac ggtaatgttg
atatgccctt cagaatgtgt gatggcatgg ttatcgacta actggcaaat tctgacacct
gcacgacatg cttcttcatc attagccgct ttgacaataa tgataaattc ttcgcccccg
tagcgataaa ccgtttcgta atcacgcgtc caactggcta gtaagttgc cagggtgcgt
aatactacat cgccgattaa atgcccgtag gtatcataa ccaatttaaa tcggtcaata
tccaacaaca ttaaataaag attcagaggc tcagcgttgc gtaactgatg atcaaaggat
tcatcaagaa cccgacgacc cggcaatccc gtcaaaacat ccatattgct acggatcgtc
agcaaataaa ttttgtaatc ggtaatgcc gcagtaaaag aaagcaaccc ctcctgaaag
gcgtcgaaat gcgcgtcctg ccagtgattt tcaacaatag ccagcattaa ttcccgacca
cagttatgca tatgttgatg ggcagaatcc attagccgaa cgtaaggtaa ttcatcgtta
tcgagtggcc ccagatgatc aatccaccga ccaaactggc acagtccata agaatggtta
tccgttattc ctggcttact ggcatctctc gcgaccacgc tgtgaaacat actcaccagc
cactggtagt gggcatcgat agccttattg agatttaaca agatggcatc aatttccgtt
gtcttcttga tcattgccac tccttttca cagttccttg tgcgcgctat tctaacgaga
gaaaagcaaa attacgtcaa tattttcata gaaatccgaa gttatgagtc atCtCtgaga
taacattgtg atttaaaaca aaatcagcgg ataaaaagt gtttaattct gtaaattacc
tctgcattat cgtaaataaa aggatgacaa atagcataac ccaataccct aatgcccag
tagttcaggc catcaggcta atttattttt atttctgcaa atgagtgacc cgaacgacgg
ccggcgcgct tttcttatcc agactgccac taatgttgat catctggtcc ggctgaactt
ctcgtccatc aaagacggcc caggaataa cgacattaat ttcaccgctc ttatcgcgaa
aaacgtaacg gtcctctcct ttgtgagaaa tcaaattacc gcgtagtgaa accgaagcgc
catcgtgcat ggttttgcg aaatcaacgg tcatttttt tgcatcatcg gttccgcgat
agccatcttc tattgcatga ggcggcggtg gcgctgcatc ctgttttaaa ccgccctggt
catctgccaa cgcataaggc atgacaagaa aacttgctaa tacaatggcc tgaaatttca
tactaactcc ttaattgcgt ttggtttgac ttattaagtc tggttgctat ttttataatt
gccaaataag aatattgcca attgttataa ggcatttaaa atcagccaac tag
```

---

What is claimed is:

1. A method comprising:
   a) obtaining multiple libraries of DNA molecules, each said library comprising clones and each said clone comprising a vector DNA sequence and an insert DNA sequence, wherein the insert DNA sequences comprise DNA obtained from a selected microorganism genome, and wherein the insert DNA sequences of each of any single library are of a same defined size and the defined size of each library is different from the defined size of any other said library;
   b) introducing each library of DNA molecules, obtained in step a), into a respective population of microorganism cells to obtain multiple populations of microorganism cells;
   c) exposing the multiple populations of microorganism cells, obtained in step b), to a condition that alters the distribution of the microorganism cell populations and the clones therein;
   d) for each of a plurality of positions along the selected genome, measuring, in the altered populations of microorganism cells obtained in step c), the amount of DNA of the insert sequences that correspond to each of the plurality of positions; and
   e) determining, from the measurements of step d), the relative amount of DNA of each insert size that corresponds to each of the plurality of genomic positions.

2. The method of claim 1, wherein the microorganism cells are selected from the group consisting of bacteria, yeast, and fungi.

3. The method of claim 1, wherein the microorganism cells are bacteria.

4. The method of claim 1, wherein the microorganism cells are Gram negative bacteria.

5. The method of claim 1, wherein the microorganism cells are E. coli.

6. The method of claim 1, wherein the organism is yeast.

7. The method of claim 1, wherein each of the multiple libraries is constructed in a vector of a type selected from the group consisting of a cosmid, a plasmid, a BAC, a YAC, a retrovirus, a bacteriophage, and a virus.

8. The method of claim 1, wherein the measuring of step d) comprises using microarray hybridization.

9. The method of claim 1, wherein the measuring of step d is at a resolution less than or equal to the smallest defined size of insert DNA sequences of step a.

10. The method of claim 1, wherein, for each defined size of insert DNA sequences, greater than 80 percent of the clones of a respective library are of the expected size.

11. The method of claim 1, wherein a genetic element from each of the multiple libraries comprises at least a portion of a genetic element that confers a selective advantage, and comparing said genetic elements pinpoints a particular genomic segment that confers the selective advantage.

12. The method of claim 1, wherein a phenotypic trait is selected from the group consisting of enhanced growth rate, decreased death, antibiotic resistance, growth in the presence of a metabolite, growth in the absence of a metabolite, enhanced growth in the presence of a toxic compound, ability to metabolize a selected substrate, ability to metabolize groups of substrates, ability to produce a selected product, ability to produce a selected intermediate, ability to produce a selected group of products and a combination thereof.

13. The method of claim 1, comprising using in step e a computer executable program designed to identify one or more genetic elements associated with a phenotypic trait, the program comprising logic to provide mathematical decomposition analysis of data from a DNA microarray hybridized with two or more genomic libraries, wherein each of the libraries comprises nucleic acid sequences of a defined size and wherein each of the libraries has a different defined size, and wherein the mathematical decomposition analysis identifies signal(s) attributable to the one or more genetic elements associated with the trait.

14. The method of claim 13, wherein the plurality of genomic libraries comprises two, three, four, five, six, seven, eight, nine, ten or more libraries.

15. The method of claim 13, wherein the mathematical decomposition analysis allows identification of a single open reading frame associated with the trait, genetic elements larger than a single open reading frame associated with the trait, operons associated with the trait, genetic elements smaller than a single open reading frame associated with the trait or a combination.

16. The method of claim 1, wherein one or more genetic elements of the insert DNA sequences of the libraries are identified using microarray hybridization in combination with a mathematical decomposition.

17. The method of claim 16, further comprising a computer executable program designed to identify one or more genetic elements associated with a trait, the program comprising: logic to provide mathematical decomposition analysis of data from a DNA microarray hybridized with two or more genomic libraries, wherein each of the libraries comprises nucleic acid sequences of a defined size, each of the libraries has a different defined size; and the mathematical decomposition analysis identifies signal(s) attributable to the one or more genetic element associated with the trait.

18. The method of claim 16, further comprising identifying genetic elements associated with a trait comprising:
   obtaining data from a DNA microarray hybridized with at least two genomic libraries, wherein each of the libraries comprises genetic elements of a defined size, each of the libraries has a different defined size; and
   conducting mathematical decomposition analysis of the data to determine a signal attributable to the trait and identify one or more genetic elements associated to the trait.

19. The method of claim 16, further comprising conducting a mathematical decomposition parallel computational analysis of data from the one or more genetic elements hybridized with two or more of said multiple libraries' insert DNA sequences, wherein the mathematical decomposition parallel computational analysis identifies signal(s) attributable to one or more of said genetic elements.

20. The method of claim 19, wherein conducting the mathematical decomposition parallel computational analysis identifies one or more of a single open reading frame associated with a trait, genetic elements larger than a single open reading frame associated with a trait, operons associated with a trait, and genetic elements smaller than a single open reading frame associated with a trait.

21. The method of claim 16, wherein the identified one or more genetic elements of the insert DNA sequences of the libraries confer or are related to a phenotypic trait.

22. The method of claim 21, further comprising conducting a wavelet based multiresolution analysis of data to identify the one or more genetic elements.

23. The method of claim 16, further comprising identifying the one or more genetic elements with a combination of a genome wide scan and a mathematical decomposition of the data into scales or signal contributions.

24. The method of claim 23, wherein the decomposed data produces unique signal intensity patterns.

25. The method of claim 24, wherein the presence of the one or more genetic elements, conferring or associated with a phenotypic trait, is indicated by any combination of signals of different scales.

26. The method of claim 25, wherein the presence of a genetic element conferring or associated with a trait is indicated by concurrent analysis of one or more signals of one or more scales.

27. The method of claim 23, wherein the mathematical decomposition comprises parallel computational analysis.

28. The method of claim 27 wherein the decomposed data produces unique signal intensity patterns.

* * * * *